(12) United States Patent
Nakanishi

(10) Patent No.: US 12,161,502 B2
(45) Date of Patent: Dec. 10, 2024

(54) X-RAY DIAGNOSIS APPARATUS AND X-RAY DIAGNOSIS METHOD

(71) Applicant: CANON MEDICAL SYSTEMS CORPORATION, Otawara (JP)

(72) Inventor: Satoru Nakanishi, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 253 days.

(21) Appl. No.: 17/809,368

(22) Filed: Jun. 28, 2022

(65) Prior Publication Data
US 2023/0000456 A1 Jan. 5, 2023

(30) Foreign Application Priority Data
Jun. 30, 2021 (JP) .................................. 2021-109228

(51) Int. Cl.
*A61B 6/50* (2024.01)
*A61B 6/00* (2006.01)
*A61B 6/03* (2006.01)
*A61B 6/46* (2024.01)

(52) U.S. Cl.
CPC ................ *A61B 6/54* (2013.01); *A61B 6/032* (2013.01); *A61B 6/4435* (2013.01); *A61B 6/465* (2013.01); *A61B 6/487* (2013.01)

(58) Field of Classification Search
CPC .......... A61B 6/54; A61B 6/032; A61B 6/4435
See application file for complete search history.

(56) References Cited

U.S. PATENT DOCUMENTS

| 2011/0040169 | A1* | 2/2011 | Kamen | G06T 7/32 600/411 |
| 2011/0158380 | A1 | 6/2011 | Tsukagoshi et al. | |
| 2012/0265050 | A1* | 10/2012 | Wang | A61B 6/485 600/407 |
| 2013/0051519 | A1 | 2/2013 | Yang et al. | |
| 2014/0161331 | A1* | 6/2014 | Cohen | G06T 11/60 382/128 |
| 2015/0036907 | A1* | 2/2015 | Seong | G06T 3/4053 382/131 |

(Continued)

FOREIGN PATENT DOCUMENTS

| JP | 2005-066037 A | 3/2005 |
| JP | 2010-178909 A | 8/2010 |

(Continued)

*Primary Examiner* — Hugh Maupin
(74) *Attorney, Agent, or Firm* — Oblon, McClelland, Maier & Neustadt, L.L.P.

(57) ABSTRACT

An X-ray diagnosis apparatus according to an embodiment includes an imaging system and a processing circuitry. The imaging system is configured to perform an imaging process on an examined subject by emitting X-rays onto the examined subject. The processing circuitry is configured to execute the imaging process on the examined subject by controlling the imaging system in an imaging mode selected from between an X-ray fluoroscopy imaging mode for obtaining an X-ray projection fluoroscopic image of the examined subject and a Computed Tomography (CT) imaging mode for obtaining a CT image of the examined subject and is configured to perform a super resolution process corresponding to the imaging mode.

18 Claims, 14 Drawing Sheets

(56) References Cited

U.S. PATENT DOCUMENTS

| | | | |
|---|---|---|---|
| 2015/0098550 A1* | 4/2015 | Yi | A61B 6/5205 |
| | | | 378/62 |
| 2015/0125061 A1* | 5/2015 | Holt | G06T 5/00 |
| | | | 382/132 |
| 2016/0232655 A1* | 8/2016 | Lachner | G06T 7/344 |
| 2018/0350112 A1* | 12/2018 | Wang | G06T 11/006 |
| 2020/0175675 A1 | 6/2020 | Ogino et al. | |
| 2021/0239626 A1* | 8/2021 | Iwao | G01N 23/046 |
| 2022/0057340 A1* | 2/2022 | Niizaka | A61B 6/00 |
| 2023/0030343 A1* | 2/2023 | Sezganov | G06T 7/246 |
| 2023/0306657 A1* | 9/2023 | Sehnert | G06T 5/70 |

FOREIGN PATENT DOCUMENTS

| | | |
|---|---|---|
| JP | 2010-240257 A | 10/2010 |
| JP | 2011-087858 A | 5/2011 |
| JP | 2011-130922 A | 7/2011 |
| JP | 2012-157691 A | 8/2012 |
| JP | 2013-158373 A | 8/2013 |
| JP | 2014-195492 A | 10/2014 |
| JP | 2019-025044 A | 2/2019 |
| JP | 2019-088380 A | 6/2019 |
| JP | 2021-013740 A | 2/2021 |

\* cited by examiner

X-RAY DIAGNOSIS APPARATUS AND X-RAY DIAGNOSIS METHOD

CROSS-REFERENCE TO RELATED APPLICATIONS

This application is based upon and claims the benefit of priority from Japanese Patent Application No. 2021-109228, filed on Jun. 30, 2021; the entire contents of which are incorporated herein by reference.

FIELD

Embodiments described herein relate generally to an X-ray diagnosis apparatus and an X-ray diagnosis method.

BACKGROUND

One of the problems to be solved by the embodiments disclosed in the present specification and drawings is to perform, while using a single X-ray Computed Tomography (CT) apparatus, both an imaging process to take a CT image and an imaging process to take a high-precision X-ray projection fluoroscopic image. However, problems to be solved by the embodiments disclosed in the present specification and drawings are not limited to this problem. It is also possible to consider problems corresponding to advantageous effects achieved by the configurations described in the embodiments below as other problems.

DETAILED DESCRIPTION

Exemplary embodiments of an X-ray diagnosis apparatus and an X-ray diagnosis method will be explained in detail below, with reference to the accompanying drawings.

First Embodiment

Figure 1:
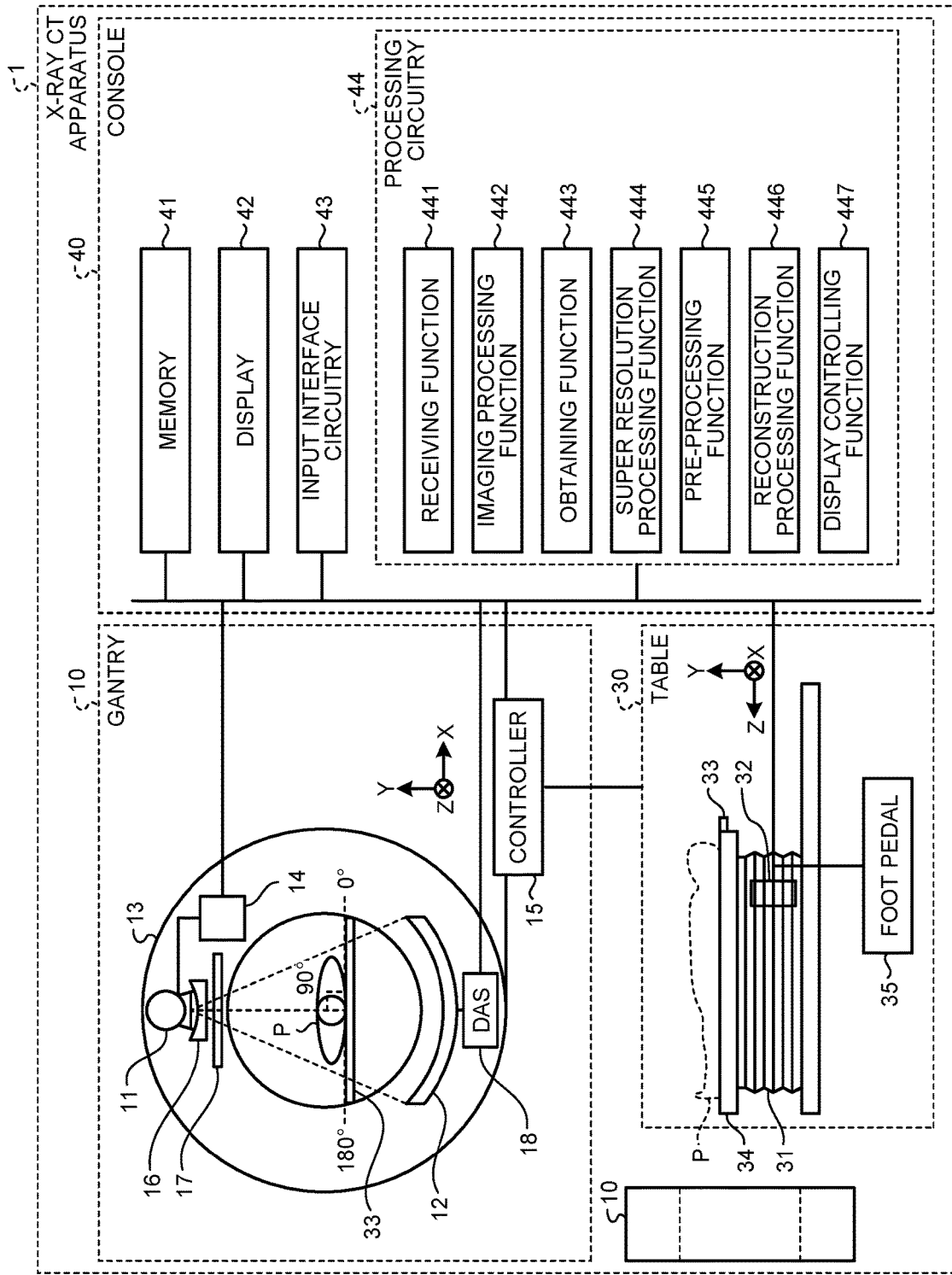
FIG. 1 is a diagram illustrating an exemplary configuration of an X-ray CT apparatus according to a first embodiment.

FIG. 1 is a diagram illustrating an exemplary configuration of an X-ray Computed Tomography (CT) apparatus (hereinafter, "X-ray CT apparatus 1") according to a first embodiment. The X-ray CT apparatus 1 is an example of an X-ray diagnosis apparatus according to the present embodiment.

As illustrated in FIG. 1, the X-ray CT apparatus 1 includes a gantry apparatus (which may be called a "gantry") 10, a table 30, and a console 40.

In the present embodiment, a rotation axis of a rotating frame 13 in a non-tilt state or the longitudinal direction of a tabletop 33 of the table 30 is defined as a Z-axis direction. Further, the axial direction orthogonal to the Z-axis direction and parallel to a floor surface is defined as an X-axis direction. Also, the axial direction orthogonal to the Z-axis direction and perpendicular to the floor surface is defined as a Y-axis direction. Although FIG. 1 depicts the gantry 10 in multiple locations for the sake of convenience in the explanation, the X-ray CT apparatus 1 in actuality includes the single gantry 10.

The gantry 10 and the table 30 are configured to operate on the basis of operations received from a user via the console 40 or operations received from the user via an operating unit provided in the gantry 10 or the table 30. The gantry 10, the table 30, and the console 40 are connected so as to be able to communicate with one another in a wired or wireless manner.

The gantry 10 is an apparatus including an imaging system configured to acquire projection data obtained by projecting an image of an examined subject (hereinafter "patient") P while using X-rays. The gantry 10 has, in a center part thereof, an opening (a bore) extending in the Z-axis direction and having a substantially circular cylindrical shape. In the opening, the tabletop 33 of the gantry 10 is inserted. In the present embodiment, having the substantially circular cylindrical shape include having a shape of which the cross-section is a perfect circle and having a shape of which the cross-section is oval. More specifically, the gantry 10 includes an X-ray tube 11 (an X-ray generating unit), a wedge 16, a collimator 17, an X-ray detector 12, an X-ray high-voltage circuitry 14, a Data Acquisition System (DAS) 18, the rotating frame 13, and a controller 15. It is assumed that the imaging system includes, at least, the X-ray tube 11 and the X-ray detector 12.

The X-ray tube 11 is a vacuum tube configured to generate the X-rays by causing thermo electrons to be emitted from a negative pole (a filament) toward a positive pole (a target or an anode), with application of high voltage and a supply of a filament current from the X-ray high-voltage circuitry 14. As a result of the thermo electrons colliding with the target, the X-rays are generated. The X-rays generated at an X-ray tube focal point of the X-ray tube 11 are, for example, formed to have a cone beam shape via the collimator 17 and are emitted onto the patient P. For instance, examples of the X-ray tube 11 include a rotating anode X-ray tube configured to generate the X-rays by having the thermo electrons emitted onto a rotating anode.

The X-ray detector 12 is configured to detect X-rays that were emitted from the X-ray tube 11 and have passed through the patient P and is configured to output an electrical signal corresponding to the amount of the X-rays to the DAS 18. Because the electrical signal detected by the X-ray detector 12 is data obtained by projecting an image of the patient P while using X-rays, the electrical signal is referred to as projection data.

For example, the X-ray detector 12 includes a plurality of rows of detecting elements in each of which a plurality of detecting elements are arranged in a channel direction along an arc while being centered on the focal point of the X-ray tube 11. Each of the plurality of detecting elements is configured to detect the amount of X-rays being incident thereto. Further, possible examples of the X-ray CT apparatus 1 include various types such as a Rotate/Rotate type (a third generation CT) in which the X-ray tube 11 and the X-ray detector 12 integrally rotate around the patient P and a Stationary/Rotate type (a fourth generation CT) in which a large number of X-ray detecting elements arrayed in a ring formation are fixed, while only the X-ray tube 11 is configured to rotate around the patient P. Any of the various types is appliable to the present embodiment.

The X-ray detector 12 according to the present embodiment includes 320 rows of detecting elements and is capable of imaging the patient P in a wide range along the body axial direction. The X-ray CT apparatus 1 including the X-ray detector 12 that has such a large number of rows of detecting elements is referred to as an Area Detector CT (ADCT) apparatus. However, the quantity of the rows of detecting elements is merely an example, and possible embodiments are not limited to this example.

The X-ray detector 12 according to the present embodiment adopts an energy integrated acquisition method. For example, the X-ray detector 12 is an indirect-conversion type detector including a grid, a scintillator array, and an optical sensor array.

The scintillator array includes a plurality of scintillators. Each of the scintillators includes a scintillator crystal that outputs light in a photon quantity corresponding to the amount of incident X-rays. The grid is arranged on a surface of the scintillator array that is positioned on the X-ray incident side and includes an X-ray blocking plate having a function of absorbing scattered X-rays. The grid may be referred to as a collimator (a one-dimensional collimator or a two-dimensional collimator) in some situations. The optical sensor array has a function of converting the light amounts from the scintillators into corresponding electrical signals and includes optical sensors configured with Photomultiplier Tubes (PMTs), for example. Alternatively, the X-ray detector 12 may be a detector of a direct conversion type that includes a semiconductor element configured to convert incident X-rays into an electrical signal.

The rotating frame 13 is configured to support the X-ray tube 11 and the X-ray detector 12 so as to be rotatable on the rotation axis. More specifically, the rotating frame 13 is an annular frame configured to support the X-ray tube 11 and the X-ray detector 12 so as to oppose each other and configured to rotate the X-ray tube 11 and the X-ray detector 12 via the controller 15 (explained later). The rotating frame 13 is rotatably supported by a fixed frame formed by using metal such as aluminum. The rotating frame 13 is configured to rotate on the rotation axis at a constant angular speed, by receiving motive power from a driving mechanism of the controller 15.

In addition to the X-ray tube 11 and the X-ray detector 12, the rotating frame 13 is configured to further support the X-ray high-voltage circuitry 14 and the DAS 18. The rotating frame 13 configured in this manner is housed in a casing having a substantially circular cylindrical shape in which the opening (the bore) serving as an imaging space is formed. The central axis of the opening matches the rotation axis of the rotating frame 13.

The X-ray high-voltage circuitry 14 includes: a high-voltage generating circuitry including electrical circuitry such as a transformer, a rectifier, and the like and having a function of generating the high voltage to be applied to the X-ray tube 11 and the filament current to be supplied to the X-ray tube 11; and an X-ray controller configured to control output voltage corresponding to the X-rays to be emitted by the X-ray tube 11. The high-voltage generating circuitry may be of a transformer type or an inverter type. Further, the X-ray high-voltage circuitry 14 may be provided on the rotating frame 13 or may be provided so as to belong to the fixed frame (not illustrated) of the gantry 10.

The rotating frame 13 is rotatably supported in a non-rotating part (e.g., the fixed frame; not illustrated in FIG. 1) of the gantry 10. A rotating mechanism includes, for example, a motor configured to generate rotating drive power and a bearing configured to transmit the rotating drive power to the rotating frame 13 so as to cause rotation. The motor is provided in the non-rotating part, for example. The bearing is physically connected to the rotating frame 13 and the motor, so that the rotating frame rotates in accordance with the rotating power of the motor.

In each of the non-rotating parts of the rotating frame 13 and of the gantry 10, a communication circuitry using a contactless method or a contact method is provided, so that units supported by the rotating frame 13 can communicate with an external device provided in the non-rotating part or the gantry 10. For example, when optical communication is adopted as the contactless communication method, the projection data generated by the DAS 18 is transmitted through optical communication, from a transmitter including a light emitting diode (LED) and being provided on the rotating frame 13, to a receiver including a photodiode and being provided in the non-rotating part of the gantry 10, and is further transferred by a transmission device from the non-rotating part to the console 40. In this situation, besides the communication method described above, it is acceptable to adopt a contactless data transfer method such as a capacitor coupling method or a radio wave method or a contact type data transfer method such as a method using a slip ring and an electrode brush. The rotating frame 13 is an example of a rotating unit.

The controller 15 includes a processing circuitry including a Central Processing Unit (CPU) or the like and a driving mechanism such as a motor and an actuator. As hardware resources, the processing circuitry includes a processor such as the CPU or a Micro Processing Unit (MPU) and memory elements such as a Read-Only Memory (ROM) and a Random Access Memory (RAM) or the like. Alternatively, for example, the controller 15 may be realized by using a processor such as a Graphics Processing Unit (GPU), an Application Specific Integrated Circuit (ASIC), or a programmable logic device (e.g., a Simple Programmable Logic Device [SPLD], a Complex Programmable Logic Device (CPLD), or a Field Programmable Gate Array [FPGA]). When the processor is a CPU, for example, the processor realizes functions by reading and executing programs saved in a memory. In contrast, when the processor is an ASIC, instead of having the programs saved in the memory, the functions are directly incorporated in the circuit of the processor as a logic circuitry. Further, the processors of the present embodiments do not each necessarily have to be structured as a single circuit. It is also acceptable to structure one processor by combining together a plurality of independent circuits so as to realize the functions thereof. In another example, it is also acceptable to integrate a plurality of constituent elements into one processor so as to realize the functions thereof.

Further, the controller 15 has a function of controlling operations of the gantry 10 and the table 30 upon receipt of an input signal from an input interface circuitry 43 attached to either the console 40 or the gantry 10. For example, under control of a processing circuitry 44 of the console 40, the controller 15 may exercise control to rotate the rotating frame 13, control to tilt the gantry 10, and control to bring the table 30 and the tabletop 33 into operation. Further, the control to tilt the gantry 10 may be realized as a result of the controller 15 turning the rotating frame 13 on an axis extending parallel to the X-axis direction, according to inclination angle (tilt angle) information input through the input interface circuitry 43 attached to the gantry 10. Further, the controller 15 may be provided for the gantry 10 or for the console 40.

The wedge 16 is a filter used for adjusting the X-ray amount of the X-rays emitted from the X-ray tube 11. More specifically, the wedge 16 is a filter configured to pass and attenuate the X-rays emitted from the X-ray tube 11, so that the X-rays emitted from the X-ray tube 11 onto the patient P has a predetermined distribution. The wedge 16 may be a wedge filter or a bow-tie filter, for example, and is a filter obtained by processing aluminum so as to have a predetermined target angle and a predetermined thickness.

The collimator 17 is configured with lead plates or the like for narrowing down the X-rays that have passed through the wedge 16 into an X-ray emission range and is configured to form a slit with a combination of the plurality of lead plates or the like.

The DAS 18 is configured to acquire the projection data detected by the X-ray detector 12 and to transfer the projection data to the console 40.

The table 30 is an apparatus on which the patient P to be scanned is placed and moved and includes a base 31, a table drive circuitry 32, the tabletop 33, a tabletop supporting frame 34, and a foot pedal 35. The base 31 is a casing configured to movably support the tabletop supporting frame 34 in vertical directions. The table drive circuitry 32 is a motor or an actuator configured to move the tabletop 33 on which the patient P is placed in the long-axis directions of the tabletop 33. The table drive circuitry 32 is configured to move the tabletop 33, in accordance with control exercised by the console 40 or control exercised by the controller 15. The tabletop 33 provided on the top face of the tabletop supporting frame 34 is a board on which the patient P is placed. In addition to moving the tabletop 33, the table drive circuitry 32 may also move the tabletop supporting frame 34 in the long-axis directions of the tabletop 33.

The foot pedal 35 is a pedal configured to receive an operation of the user to cause the X-rays to be emitted in X-ray imaging processes. For example, when the user performs an operation to cause the X-rays to be emitted by stepping on the foot pedal 35, a signal indicating an input of the operation is transmitted from the foot pedal 35 to the console 40 or the controller 15. The foot pedal 35 is an example of an operating unit according to the present embodiment. Possible embodiments of the operating unit configured to receive the operation of the user to cause the X-rays to be emitted are not limited to the foot pedal 35, and it is also acceptable to use a button operable with a hand, a touch panel, or the like. Further, the operating unit may be provided for the gantry 10 or the console 40, instead of for the table 30. Further, the table 30 may further include another operating unit for receiving operations of the user to adjust the height and the tilt of the tabletop 33. This operating unit is omitted from the drawings.

The console 40 is an apparatus configured to control the gantry 10 and to generate CT image data or the like on the basis of a result of a scan performed by the gantry 10. The console 40 includes a memory 41 (a storage unit), a display (a display unit), the input interface circuitry 43 (an input unit), and the processing circuitry 44 (a processing unit). Data communication among the memory 41, the display 42, the input interface circuitry 43, and the processing circuitry 44 is performed via a bus.

The memory 41 is a storage device such as a Hard Disk Drive (HDD), a Solid State Drive (SSD), or an integrated circuit storage device configured to store therein various types of information. The memory 41 is configured to store therein, for example, the projection data and reconstructed image data. Other than an HDD or an SSD, the memory 41 may be a drive device configured to read and write various types of information from and to a portable storage medium such as a Compact Disc (CD), a Digital Versatile Disc (DVD), or a flash memory or a semiconductor memory element such as a Random Access Memory (RAM). Further, the storage area of the memory 41 may be inside the X-ray CT apparatus 1 or may be inside an external storage device connected via a network. Further, the memory 41 has stored therein a control program according to the present embodiment.

Further, the memory 41 is configured to store therein the projection data acquired by the imaging system and the CT image data obtained by reconstructing acquired data.

The display 42 is configured to display various types of information. For example, the display 42 is configured to output medical images generated by the processing circuitry 44, a Graphical User Interface (GUI) for receiving various types of operations from an operator, and the like. In the present embodiment, the medical images displayed on the display 42 are a cross-sectional image of the patient P based on the CT image data and an X-ray projection fluoroscopic image based on the projection data.

Further, for example, it is possible to use, as the display 42, a Liquid Crystal Display (LCD) device, a Cathode Ray Tube (CRT) display, an Organic Electroluminescence Display (OELD), a plasma display, or other arbitrary displays, as appropriate. Further, the display 42 may be provided for the gantry 10. Furthermore, the display 42 may be of a desktop type or may be configured by using a tablet terminal or the like capable of wirelessly communicating with the main body of the console 40.

The input interface circuitry 43 is configured to receive various types of input operations from the user, to convert the received input operations into electrical signals, and to output the electrical signals to the processing circuitry 44. For example, the input interface circuitry 43 is configured to receive, from the operator, an acquisition condition used at the time of acquiring the projection data, a reconstruction condition used at the time of reconstructing the CT image data, and the like. For example, it is possible to use, as the input interface circuitry 43, a mouse, a keyboard, a trackball, a switch, a button, a joystick, a touchpad, and a touch panel display, and/or the like, as appropriate.

Further, in the present embodiment, the input interface circuitry 43 does not necessarily have to include physical operation component parts such as a mouse, a keyboard, a trackball, a switch, a button, a joystick, a touchpad, a touch panel display, and/or the like. For instance, possible examples of the input interface circuitry 43 include an electrical signal processing circuit configured to receive an electrical signal corresponding to an input operation from an external input device provided separately from the apparatus and to output the electrical signal to the processing circuitry 44. Further, the input interface circuitry 43 is an example of an operating unit or an input unit.

Alternatively, the input interface circuitry 43 may be provided for the gantry 10. For example, the foot pedal 35 described above may serve as the input interface circuitry 43. Further, the input interface circuitry 43 may be configured by using a tablet terminal or the like capable of wirelessly communicating with the main body of the console 40.

The processing circuitry 44 is configured to control operations of the entirety of the X-ray CT apparatus 1, in accordance with the electrical signals corresponding to the input operations output from the input interface circuitry 43. For example, the processing circuitry 44 includes a receiving function 441, an imaging processing function 442, an obtaining function 443, a super resolution processing function 444, a pre-processing function 445, a reconstruction processing function 446, and a display controlling function 447. In this situation, for example, processing functions implemented by the constituent elements of the processing circuitry 44 illustrated in FIG. 1, namely, the receiving function 441, the imaging processing function 442, the obtaining function 443, the super resolution processing function 444, the pre-processing function 445, the reconstruction processing function 446, and the display controlling function 447, are recorded in the memory 41 in the form of computer-executable programs. For example, the processing circuitry 44 is a processor and is configured to read and execute the programs from the memory 41 so as to realize the functions corresponding to the read programs. In other words, the processing circuitry 44 that has read the programs has the functions illustrated within the processing circuitry 44 in FIG. 1. For example, the memory 41 is an example of a storage medium configured with a non-transitory computer-readable medium and including instructions to be executed by a computer. The receiving function 441 is an example of a receiving unit. The imaging processing function 442 is an example of an imaging processing unit. The obtaining function 443 is an example of an obtaining unit. The super resolution processing function 444 is an example of a super resolution processing unit. The pre-processing function 445 is an example of a pre-processing unit. The reconstruction processing function 446 is an example of a reconstruction processing unit. The display controlling function 447 is an example of a display controlling unit and an output unit.

Although FIG. 1 illustrates the example in which the single processing circuit (i.e., the processing circuitry 44) realizes the receiving function 441, the imaging processing function 442, the obtaining function 443, the super resolution processing function 444, the pre-processing function 445, the reconstruction processing function 446, and the display controlling function 447, possible embodiments are not limited to this example. For instance, the processing circuitry 44 may be structured by combining together a plurality of independent processors, so that the processing functions are realized as a result of the processors executing the programs. Further, the processing functions included in the processing circuitry 44 may be realized as being distributed among or integrated into one or more processing circuits, as appropriate.

The receiving function 441 is configured to receive various types of operations of the user via the input interface circuitry 43, the foot pedal 35, and other operating units. For example, the receiving function 441 is configured to receive a user operation to press an operating button displayed on the display 42. Further, the receiving function 441 is configured to receive an operation of the user to select an imaging mode (explained later) and an operation to instruct that a super resolution process be executed. Further, the receiving function 441 is configured to receive, via the foot pedal 35 or the like, user operations to start and end imaging processes.

The imaging processing function 442 is configured to execute an imaging process on the patient P, by controlling the imaging system. More specifically, the imaging processing function 442 is configured to control the process performed by the gantry 10 to acquire the X-rays that have passed the patient P, by controlling operations of the X-ray high-voltage circuitry 14, the X-ray detector 12, the controller 15, the DAS 18, and the table drive circuitry 32.

The imaging processing function 442 according to the present embodiment is capable of executing the imaging process on the patient P, in at least two mutually-different imaging modes. More specifically, the imaging processing function 442 is configured to execute the imaging process on the patient P, by controlling the imaging system in an imaging mode selected from between an X-ray fluoroscopy imaging mode and a CT imaging mode, in accordance with a selection made by the user.

The X-ray fluoroscopy imaging mode is a mode for obtaining an X-ray projection fluoroscopic image of the patient P. X-ray projection fluoroscopic image data is projection data obtained as a result of the X-ray detector 12 acquiring X-rays emitted by the X-ray tube 11 from a prescribed position. The X-ray projection fluoroscopic image is a fluoroscopic image based on the projection data acquired in the X-ray fluoroscopy imaging mode. In the present embodiment, the projection data that has not been reconstructed is used as two-dimensional X-ray projection fluoroscopic image data. The X-ray fluoroscopy imaging mode is an example of the second imaging mode. The X-ray projection fluoroscopic image may simply be referred to as a projection fluoroscopic image.

In the X-ray fluoroscopy imaging mode, the prescribed position in which the X-ray tube 11 emits the X-rays onto the patient P may be, for example, a position straight above the patient P, as illustrated in FIG. 1. The position of the X-ray tube 11 may be referred to as a view position and is expressed with an angle in the range of 0° to 360°. For example, when the X-ray tube 11 is positioned straight above the patient P, the view position of the X-ray tube 11 is 90°. However, the prescribed position is not limited to this example and may be set by the user.

In the X-ray fluoroscopy imaging mode, the X-ray tube 11 may be in a state of being fixed in the prescribed position, while the rotating frame 13 of the X-ray CT apparatus 1 does not rotate during the imaging process. Alternatively, while the rotating frame 13 is rotating during the imaging process, X-rays may be emitted at the time when the X-ray tube 11 reaches the prescribed position. Further, in the X-ray fluoroscopy imaging mode, the tabletop 33 is not moved while X-rays are being emitted from the X-ray tube 11.

Figure 2:
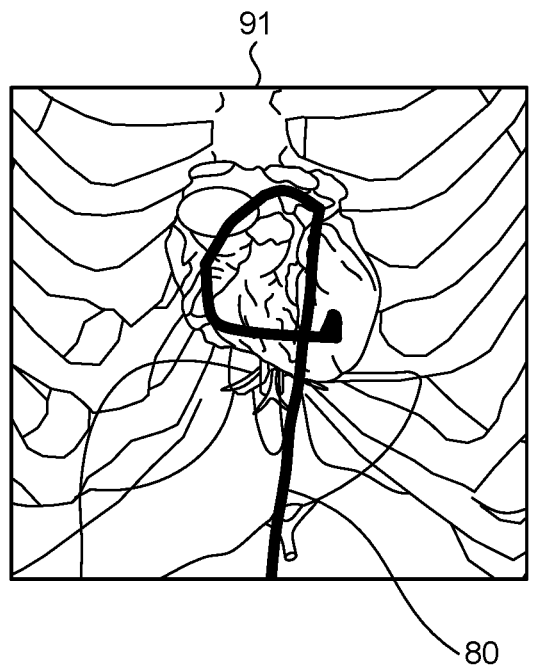
FIG. 2 is an example of X-ray projection fluoroscopic image data according to the first embodiment.

FIG. 2 is an example of projection data 91 according to the first embodiment. In the present embodiment, the projection data 91 being displayed on the display 42 (explained later) will be referred to as an X-ray projection fluoroscopic image.

X-ray fluoroscopic images are used, for example, for visually recognizing, during intervention treatment, the position of a device inserted in the body of the patient P for whom a medical doctor is implementing manipulation, or the like. For example, in the example of FIG. 2, a catheter 80 inserted in the heart of the patient P is rendered in the projection data 91, together with bones and organs of the patient P. In the present embodiment, X-ray fluoroscopic images are assumed to be two-dimensional still images.

The CT imaging mode is a mode for obtaining a CT image of the patient P. In other words, in the CT imaging mode, the imaging processing function 442 is configured to execute an imaging process to generate commonly-used CT image data. Accordingly, in the CT imaging mode, it is also possible to move the tabletop 33 while X-rays are being emitted from the X-ray tube 11 depending on the imaging method. The CT image data is data obtained as a result of the reconstruction processing function 446 (explained later) reconstructing the projection data. Further, for example, the CT image is a two-dimensional cross-sectional image or a three-dimensional image based on the CT image data that is displayed on the display 42 by the display controlling function 447 (explained later).

For example, in the CT imaging mode, the imaging processing function 442 is configured to cause the imaging system to perform the process of imaging the patient P while the rotating frame 13 is rotating. In this situation, the CT imaging mode is an example of the first imaging mode.

Figure 3:
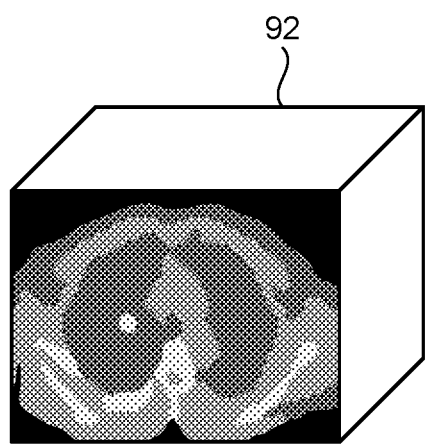
FIG. 3 is an example of CT image data according to the first embodiment.

FIG. 3 is an example of CT image data 92 according to the first embodiment. For example, as illustrated in FIG. 3, the CT image data 92 is three-dimensional volume data. On the basis of the CT image data 92, the display controlling function 447 (explained later) is configured to cause the display 42 to display a CT image which is an arbitrary cross-sectional image or a three-dimensional image, according to a designation by the user or the like.

The imaging processing function 442 is configured to control the imaging system so as to image the patient P in an imaging mode selected from between the X-ray fluoroscopy imaging mode and the CT imaging mode, in accordance with a selection made by the user and received by the receiving function 441.

Further, when performing the imaging process in the CT imaging mode, the imaging processing function 442 may further take a scanogram image (a position determining image).

The position determining image is an image for setting an imaging range of a diagnosis-purpose CT image. Further, the imaging process for obtaining the position determining image is referred to as a position determining imaging process. Generally speaking, the position determining image is a two-dimensional image. To distinguish a normal CT image from the position determining image, the normal CT image may be referred to as a "diagnosis-purpose CT image".

In the position determining imaging process, the imaging processing function 442 is configured to perform the imaging process by using an imaging method different from that in the X-ray fluoroscopy imaging mode. More specifically, as described above, in the X-ray fluoroscopy imaging mode, the tabletop 33 does not move while the X-rays are being emitted from the X-ray tube 11; however, when the position determining imaging process is performed while the CT imaging mode is used, the tabletop 33 moves while X-rays are being emitted.

For example, while performing the position determining imaging process, the imaging processing function 442 is configured to move the tabletop 33 of the table 33, while the rotating frame 13 (a gantry rotating unit) of the gantry 10 is in a non-rotating state. Further, during the position determining imaging process, the imaging processing function 442 is configured to perform data acquisition that uses only the vicinity of a central part of the X-ray detector 12 in terms of the Z-axis direction. More specifically, the imaging processing function 442 is configured to perform the imaging process with a narrowed X-ray emission range, by controlling the collimator 17 positioned directly beneath the X-ray tube 11, so that the X-ray are emitted only onto the vicinity of the central part of the X-ray detector 12 in terms of the Z-axis direction.

Further, according to another method for performing the position determining imaging process, a three-dimensional position determining image may be taken. This method may be referred to as three-dimensional (3D) scanography by which a CT scan is performed by using an X-ray dose lower than that used in a CT imaging process to obtain a diagnosis-purpose CT image. When performing the three-dimensional position determining imaging process, the imaging processing function 442 uses a similar imaging method to the method in CT image taking processes in the CT imaging mode, except for the dose of the X-rays. The imaging processing function 442 may obtain the three-dimensional position determining image of the patient P by using the three-dimensional position determining imaging process as described herein.

Further, the imaging processing function 442 may perform only the diagnosis-purpose CT image taking process, without performing the position determining imaging process.

Returning to the description of FIG. 1, the obtaining function 443 is configured to obtain the projection data acquired by the imaging system. More specifically, the obtaining function 443 is configured to obtain the projection data transferred thereto from the DAS 18 and to save the obtained projection data in the memory 41.

The super resolution processing function 444 is configured to perform a super resolution process corresponding to the imaging mode on one of the projection data 91 and the CT image data 92. More specifically, the super resolution processing function 444 is configured to switch between the types of data on which the super resolution process is to be performed, depending on which mode was used by the imaging processing function 442 for imaging the patient P, between the X-ray fluoroscopy imaging mode and the CT imaging mode. In this situation, the super resolution process performed on the projection data 91 may be referred to as a super resolution process of a projection data domain. The super resolution process performed on the CT image data 92 may be referred to as a super resolution process of a CT image domain.

For example, when the imaging processing function 442 performed the imaging process on the patient P in the X-ray fluoroscopy imaging mode, the super resolution processing function 444 is configured to perform the super resolution process on the projection data 91. In the present embodiment, the super resolution processing function 444 uses the projection data 91 on which a pre-processing process has been performed by the pre-processing function 445 (explained later) as data subject to the super resolution process.

Further, in the present embodiment, both the data detected by the X-ray detector 12 and on which the pre-processing process has not been performed and the data on which the pre-processing process has been performed by the pre-processing function 445 (explained later) are referred to as the projection data 91; however, the data prior to the pre-processing process may be referred to as detection data to make a distinction.

Further, when the imaging processing function 442 performed the imaging process on the patient P in the CT imaging mode, the super resolution processing function 444 is configured to perform the super resolution process on the CT image data 92.

Possible methods used for the super resolution process are not particularly limited, and a publicly-known method may be used. For example, the super resolution processing function 444 may perform the super resolution process on one of the projection data 91 and the CT image data 92, by using a trained model that has learned, through machine learning, low resolution data/images and high resolution data/images.

For example, when the super resolution process is to be performed on the projection data 91, a plurality of training pairs are prepared, each training pair being made up of low resolution projection data serving as input information and high resolution projection data serving as target (supervisor) information, so as to obtain a trained model for the projection data 91 by training a machine learning model such as a Convolutional Neural Network (CNN). The low resolution projection data may be obtained by imaging the patient P or a phantom or may be obtained by applying a resolution lowering process to high resolution data obtained by imaging the patient P or a phantom. Similarly, the high resolution projection data may be obtained by imaging the patient P or a phantom or may be obtained by applying a resolution enhancing process to low resolution projection data obtained by imaging the patient P or a phantom. For example, high quality projection data may be high quality projection data obtained by implementing the focal point controlling method described later or may be X-ray projection data taken by using a high definition X-ray detector having a small pixel pitch.

Normally, the pixel pitch of planar X-ray detectors used in C-arm X-ray imaging apparatuses and the like is smaller than the pixel pitch of curved X-ray detectors used in CT. Accordingly, it is possible to perform a process of converting an image from such a planar X-ray detector into an image taken by a curved X-ray detector for CT so as to use the image as target information. In that situation, according to one possible embodiment, a super resolution model is obtained by training a machine learning model by using high quality projection data taken with the focal point control as target information and using relatively low quality projection data taken without the focal point control as input information, so as to apply the super resolution model to relatively low quality projection data taken without the focal point control.

In another example, it is also possible to apply an image quality enhancing process with the focal point control to each of high resolution and low resolution projection data. In that situation, for example, it is possible to use, as the projection data serving as high resolution target information, projection data taken by using the high definition X-ray detector described above.

Further, in place of the learning process using only the X-ray projection data, it is also possible to use a transfer learning method. It is possible to obtain a super resolution trained model by using a super resolution model trained with optical images, Magnetic Resonance Imaging (MRI) images, or the like that are not X-ray projection data as a base and further causing the super resolution model to learn X-ray projection data by using the abovementioned method. Alternatively, it is also possible, for example, to obtain a super resolution trained model by using a training algorithm that does not use supervisor information, by using, as a model, an auto encoder network, in which an encoder network and a decoder network are connected in series.

Similarly, when the super resolution process is to be performed on the CT image data 92, a plurality of training pairs are prepared, each training pair being made up of low resolution CT image data serving as input information and high resolution CT image data serving as target information, so as to obtain a trained model for projection data by training a machine learning model such as a Convolutional Neural Network (CNN). The low resolution CT image data may be obtained by reconstructing projection data obtained by imaging the patient P or a phantom, may be obtained by applying a resolution lowering process to high resolution CT image data obtained by imaging the patient P or a phantom, may be CT image data reconstructed after applying a resolution lowering process to high resolution projection data, or may be a result of a resolution lowering process incorporated in the process of reconstructing a CT image from high resolution projection data.

Similarly, the high resolution CT image data may be obtained by reconstructing projection data obtained by imaging the patient P or a phantom, may be obtained by applying a resolution enhancing process to low resolution CT image data obtained by imaging the patient P or a phantom, may be CT image data reconstructed after applying a resolution enhancing process to low resolution projection data, or may be a result of a resolution enhancing process incorporated in the process of reconstructing a CT image from high resolution projection data.

The projection data at the time of reconstructing the abovementioned CT image data may be projection data obtained through the method described above in the explanation about the super resolution model training method for a projection database.

Further, in place of the learning process using only the X-ray projection data, it is also possible use a transfer learning method. It is possible to obtain a super resolution trained model by using a super resolution model trained with optical images, MRI images, or the like that are not CT image data as a base and further training the model while using CT image data as described above. Furthermore, it is also possible, for example, to obtain a super resolution trained model by using a training algorithm that does not use supervisor information, by using, as a model, an auto encoder network in which an encoder network and a decoder network are connected in series.

The trained model may be stored in the memory 41, for example, or may be incorporated in the super resolution processing function 444 by way of a hardware installation using an FPGA, for example. More specifically, it is assumed that both a trained super resolution model to be used in the X-ray fluoroscopy imaging mode and a trained super resolution model to be used in the CT imaging mode are either stored in the memory 41 or incorporated in the super resolution processing function 444. Further, the super resolution processing function 444 may vary the content of the super resolution process to be applied, between the X-ray fluoroscopy imaging mode and the CT imaging mode.

Further, when an operation is performed by the user to instruct that the super resolution process be executed, the super resolution processing function 444 is configured to execute the super resolution process.

The super resolution processing function 444 is configured to save, in the memory 41, the projection data 91 or the CT image data 92 on which the super resolution process has been performed.

On the acquired projection data 91, the pre-processing function 445 is configured to perform a pre-processing process such as a logarithmic conversion process, an offset correction process, an inter-channel sensitivity correction process, a beam hardening correction, and/or the like. Further, the content of the pre-processing process may be different between when the imaging process was executed in the X-ray fluoroscopy imaging mode and when the imaging process was executed in the CT imaging mode. In another example, the pre-processing function 445 may be configured not to perform the pre-processing process on the projection data 91 when the imaging process was executed in the X-ray fluoroscopy imaging mode.

The reconstruction processing function 446 is configured to generate the CT image data 92 by reconstructing the projection data 91. In this situation, it is assumed that the reconstruction processing function 446 in the present embodiment is configured to reconstruct the projection data 91 on which the pre-processing process has been performed by the pre-processing function 445. For example, in the reconstructing process, the reconstruction processing function 446 is configured to implement a Filtered Back Projection (FBP) method or a successive approximation reconstruction method.

Further, when the imaging process was executed in the X-ray fluoroscopy imaging mode, the X-ray CT apparatus 1 according to the present embodiment is configured to output an X-ray projection fluoroscopic image based on the projection data acquired in the X-ray fluoroscopy imaging mode for one or both of a display purpose and an analysis purpose. Further, when the imaging process was executed in the CT imaging mode, the X-ray CT apparatus 1 is configured to output a CT image reconstructed on the basis of the projection data acquired in the CT imaging mode for one or both of a display purpose and an analysis purpose.

More specifically, the display controlling function 447 is configured to cause the display 42 to display a medical image based on one of the projection data 91 and the CT image data 92 on which the super resolution process has been performed by the super resolution processing function 444.

For example, when the patient P was imaged in the X-ray fluoroscopy imaging mode, the display controlling function 447 is configured to cause the display 42 to display the projection data 91 on which the super resolution process has been performed, as an X-ray projection fluoroscopic image. In contrast, when the patient P was imaged in the CT imaging mode, the display controlling function 447 is configured to cause the display 42 to display a CT image based on the CT image data 92 on which the super resolution process has been performed.

Furthermore, the display controlling function 447 is configured to cause the display 42 to display a GUI that can be operated by the user.

For example, the display controlling function 447 is configured to cause the display 42 to display an imaging mode selecting screen on which the user is able to select which mode is to be used for imaging the patient P between the X-ray fluoroscopy imaging mode and the CT imaging mode.

Figure 4:
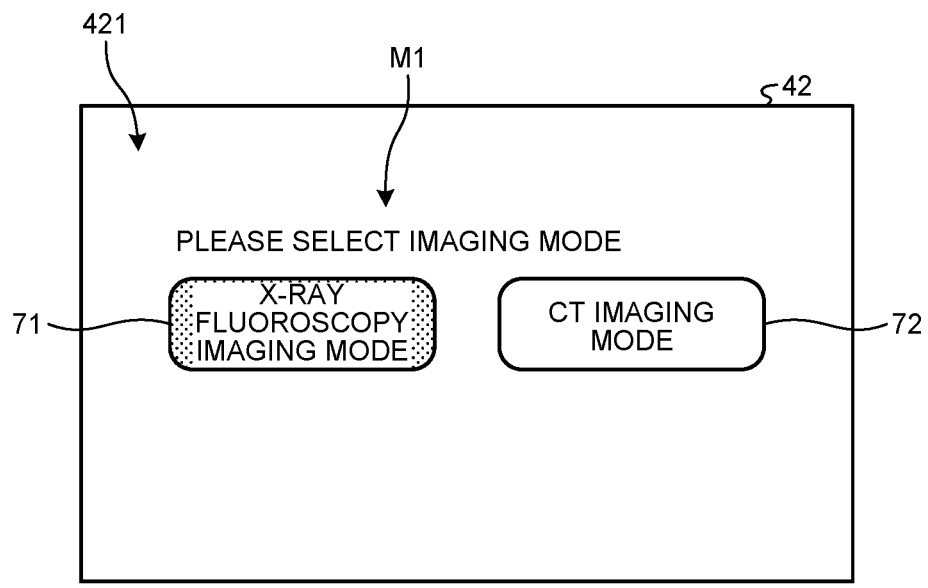
FIG. 4 is a drawing illustrating an example of an imaging mode selecting screen according to the first embodiment.

FIG. 4 is a drawing illustrating an example of an imaging mode selecting screen 421 according to the first embodiment. As illustrated in FIG. 4, the imaging mode selecting screen 421 includes an X-ray fluoroscopy imaging mode selecting button 71 and a CT imaging mode selecting button 72.

The X-ray fluoroscopy imaging mode selecting button 71 is an image button configured to receive a user operation to select the X-ray fluoroscopy imaging mode. Further, the CT imaging mode selecting button 72 is an image button configured to receive a user operation to select the CT imaging mode. In an example, the display controlling function 447 may display, in a distinguishable manner, which mode is currently selected from between the X-ray fluoroscopy imaging mode and the CT imaging mode, by using a certain display mode such as the color of the X-ray fluoroscopy imaging mode selecting button 71 and the CT imaging mode selecting button 72. In the example in FIG. 4, it is assumed that the X-ray fluoroscopy imaging mode selecting button 71 has been pressed by the user.

Further, the display controlling function 447 may also display, on the imaging mode selecting screen 421, a message Ml to explain the operation such as "Please select an imaging mode". The configuration of the imaging mode selecting screen 421 illustrated in FIG. 4 is merely an example, and possible embodiment are not limited to this example. Further, the imaging mode selecting screen 421 may also serve as another input operation screen.

Further, the display controlling function 447 is configured to cause the display 42 to display a super resolution process operation screen on which the user is able to select whether or not the super resolution process is to be performed in the X-ray fluoroscopy imaging mode and in the CT imaging mode.

Figure 5:
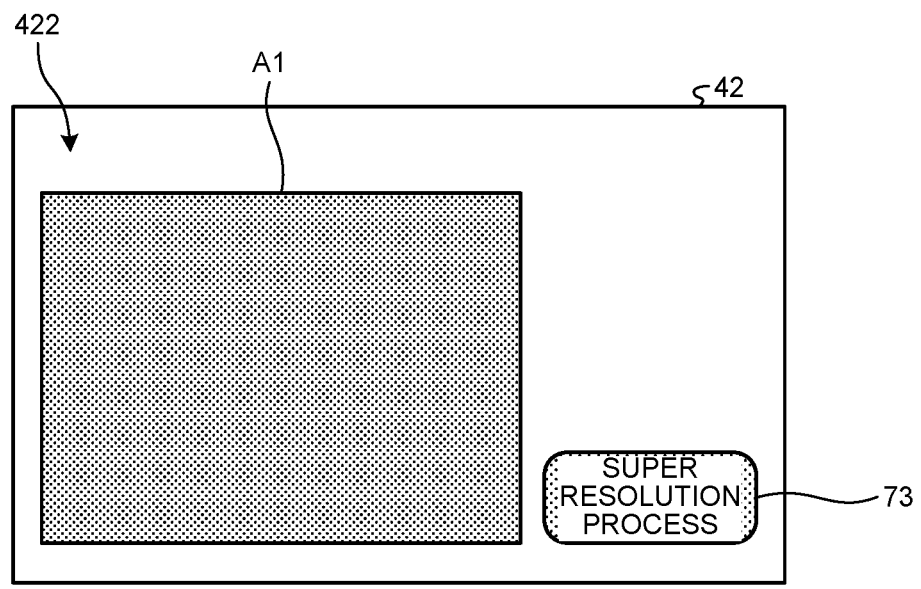
FIG. 5 is a drawing illustrating an example of a super resolution process operation screen according to the first embodiment.

FIG. 5 is a drawing illustrating an example of a super resolution process operation screen 422 according to the first embodiment. As illustrated in FIG. 5, the super resolution process operation screen 422 includes, for example, an image display area A1 and a super resolution process execution button 73.

The super resolution process execution button 73 is an image button configured to be able to receive a user operation to select whether or not the super resolution process is to be executed. For example, when the user presses the super resolution process execution button 73, a function of the super resolution process performed by the super resolution processing function 444 is turned on. In contrast, when the user has not pressed the super resolution process execution button 73, the function of the super resolution process performed by the super resolution processing function 444 is turned off. In an example, a button to turn on the super resolution processing function and another button to turn off the super resolution processing function may separately be provided. Further, the display controlling function 447 is configured to display, in a distinguishable manner, whether the super resolution processing function is on or off, by using a certain display mode such as the color of the super resolution process execution button 73. Additionally, the display controlling function 447 may display text "on" or "off", over the super resolution process execution button 73 or in the vicinity of the super resolution process execution button 73.

In the present embodiment, it is assumed that the display mode of the super resolution process execution button 73 is the same for both the X-ray fluoroscopy imaging mode and the CT imaging mode. In other words, the super resolution process execution button 73 is displayed in the same mode regardless of which mode is selected from between the X-ray fluoroscopy imaging mode and the CT imaging mode.

Accordingly, depending on which mode is selected by the user from between the X-ray fluoroscopy imaging mode and the CT imaging mode, the data subject to the super resolution process represented by the super resolution process execution button 73 is different. For example, while the X-ray fluoroscopy imaging mode is selected by the user, when the user presses the super resolution process execution button 73, the operation denotes an operation to turn on a super resolution process to be performed on the projection data 91. In contrast, while the CT imaging mode is selected by the user, when the user presses the super resolution process execution button 73, the operation denotes an operation to turn on a super resolution process to be performed on the CT image data 92.

For example, while the X-ray fluoroscopy imaging mode is selected, when the user has not pressed the super resolution process execution button 73, the display controlling function 447 causes the projection data 91 prior to the super resolution process to be displayed in an image display area A1. In contrast, while the X-ray fluoroscopy imaging mode is selected, when the user presses the super resolution process execution button 73, the display controlling function 447 causes the projection data 91 after the super resolution process to be displayed in the image display area A1.

Further, while the CT imaging mode is selected, when the user has not pressed the super resolution process execution button 73, the display controlling function 447 causes a CT image based on the CT image data 92 prior to the super resolution process to be displayed in the image display area A1. In contrast, while the CT imaging mode is selected, when the user presses the super resolution process execution button 73, the display controlling function 447 causes a CT image based on the CT image data 92 after the super resolution process to be displayed in the image display area A1.

Further, prior to an imaging process, the user may select, in advance, whether the super resolution process is to be on or off. For example, a single operation screen may allow the user to select an imaging mode and whether the super resolution process is on or off.

Figure 6:
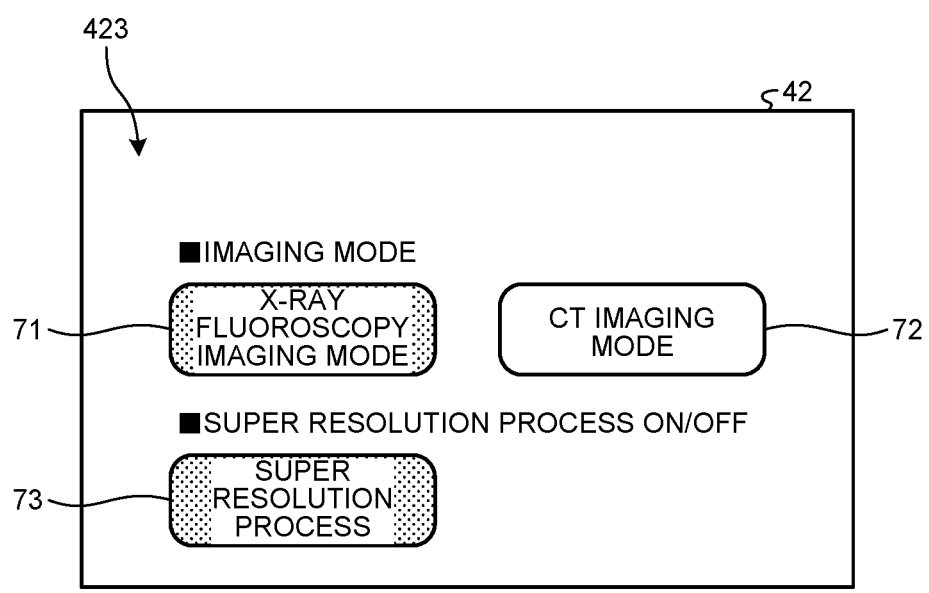
FIG. 6 is a drawing illustrating an example of an operation screen in another mode according to the first embodiment.

FIG. 6 is a drawing illustrating an example of an operation screen in another mode according to the first embodiment. On an operation screen 423 in FIG. 6, the single screen displays the X-ray fluoroscopy imaging mode selecting button 71, the CT imaging mode selecting button 72, and the super resolution process execution button 73. The timing with which the operation screen 423 is displayed may be, for example, before an imaging process is started. When the super resolution process execution button 73 is displayed at the same time as the X-ray fluoroscopy imaging mode selecting button 71 and the CT imaging mode selecting button 72, as observed on the operation screen 423, the user can also select whether the super resolution process is to be on or off, at the time of selecting an imaging mode before the imaging process is started.

Next, a flow in an imaging process performed by the X-ray CT apparatus 1 according to the present embodiment configured as described above will be explained.

Figure 7:
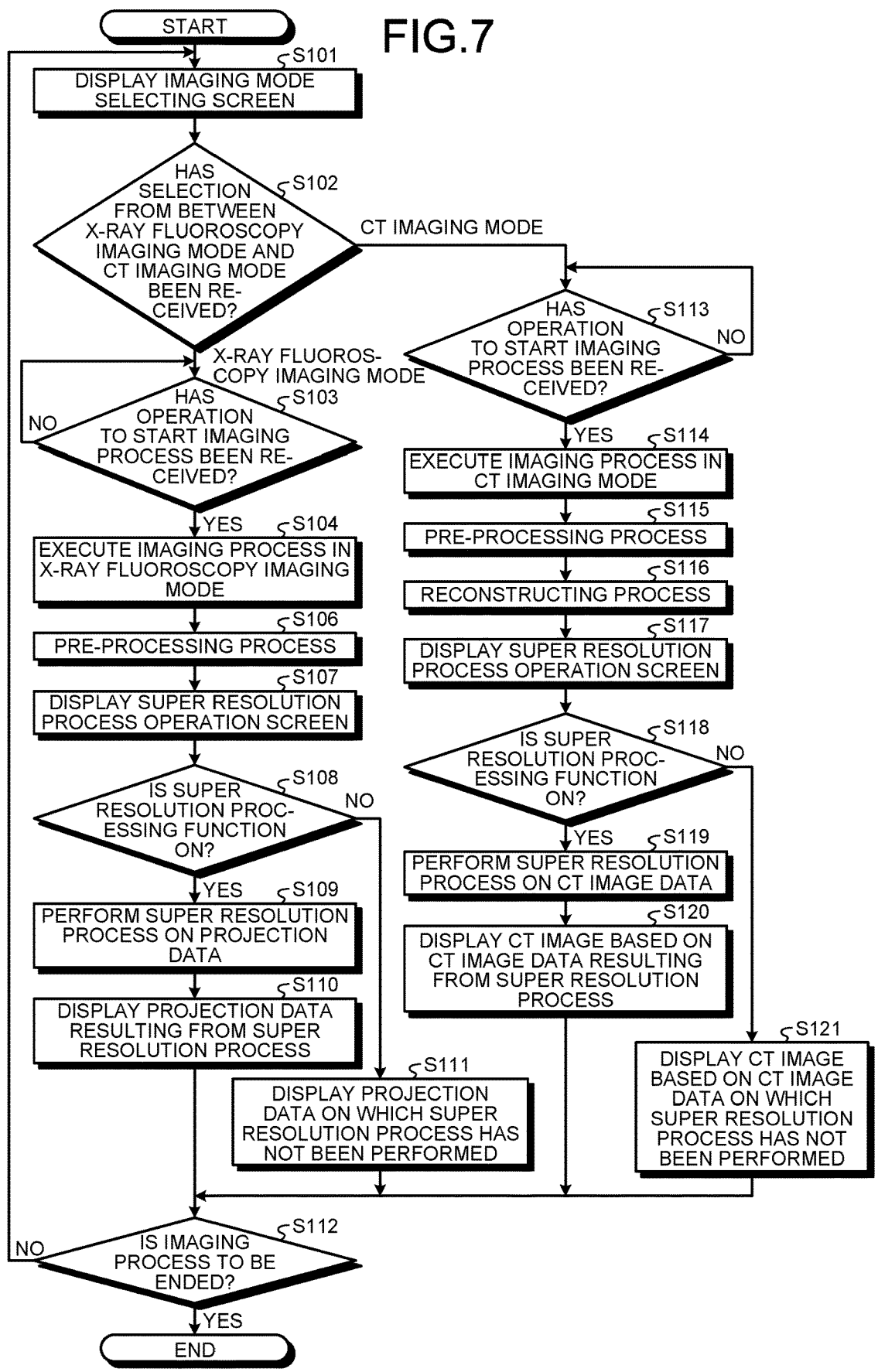
FIG. 7 is a flowchart illustrating an example of a flow in an imaging process performed by the X-ray CT apparatus according to the first embodiment.

FIG. 7 is a flowchart illustrating an example of the flow in the imaging process performed by the X-ray CT apparatus 1 according to the first embodiment.

At first, the display controlling function 447 causes the display 42 to display the imaging mode selecting screen 421 (step S101).

Subsequently, the receiving function 441 receives a user operation to select which mode is used for imaging the patient P between the X-ray fluoroscopy imaging mode and the CT imaging mode (step S102).

For example, when the user presses the X-ray fluoroscopy imaging mode selecting button 71 on the imaging mode selecting screen 421, the receiving function 441 receives an indication that the X-ray fluoroscopy imaging mode was selected by the user (step S102: "X-ray fluoroscopy imaging mode").

After that, the receiving function 441 judges whether or not a user operation to start the imaging process has been received via the foot pedal 35, a touch panel, or the like (step S103). In an example, the display controlling function 447 may display, on the imaging mode selecting screen 421, an imaging start button capable of receiving a user instruction to start the imaging process.

When a user operation to start the imaging process has not been received (step S103: No), the receiving function 441 waits for the user operation.

After that, when the receiving function 441 receives a user operation to start the imaging process (step S103: Yes), the imaging processing function 442 executes the imaging process in the X-ray fluoroscopy imaging mode (step S104). For example, under control of the imaging processing function 442, the controller 15 controls operations of the gantry 10 and the table 30, so that the X-ray tube 11 emits X-rays onto the patient P from the prescribed position. Further, the X-ray detector 12 detects X-rays that were emitted from the X-ray tube 11 and have passed through the patient P and further outputs the electrical signal corresponding to the amount of the X-rays to the DAS 18 as the projection data. The DAS 18 transmits the projection data 91 to the console 40. The obtaining function 443 obtains the projection data 91 transmitted thereto from the DAS 18.

Subsequently, the pre-processing function 445 performs the pre-processing process on the projection data 91 obtained by the obtaining function 443 (step S106).

After that, the display controlling function 447 causes the display 42 to display the super resolution process operation screen 422 (step S107).

Further, the receiving function 441 judges whether or not a user operation to turn on the super resolution processing function has been received (step S108). In this situation, the timing for receiving the user operation to turn on or off the super resolution processing function does not necessarily have to be at step S108. As explained with reference to FIG. 6, the user operation may be received prior to the execution of the imaging process.

When the receiving function 441 receives a user operation to turn on the super resolution processing function (step S108: Yes), the super resolution processing function 444 performs a super resolution process on the pre-processed projection data 91 (step S109).

After that, the display controlling function 447 causes the display 42 to display the projection data 91 resulting from the super resolution process (step S110).

On the contrary, when the receiving function 441 has not received a user operation to turn on the super resolution processing function (step S108: No) or when the receiving function 441 has received a user operation to turn off the super resolution processing function, the display controlling function 447 causes the display 42 to display the pre-processed projection data 91 on which the super resolution process has not been performed, as an X-ray projection fluoroscopic image (step S111).

After that, when the receiving function 441 has not received an operation to end the imaging process (step S112: No), the process returns to step S101 where a processing mode is selected, so that the processes are repeated. Alternatively, while the X-ray fluoroscopy imaging mode is maintained, the process may return to step S103 where an operation to start an imaging process is waited for.

Further, when the user presses the CT imaging mode selecting button 72 on the imaging mode selecting screen 421, the receiving function 441 receives an indication that the CT imaging mode was selected by the user (step S102: the CT imaging mode).

After that, the receiving function 441 judges whether or not a user operation to start the imaging process has been received via the foot pedal 35, a touch panel, or the like (step S113).

When a user operation to start the imaging process has not been received (step S113: No), the receiving function 441 waits for the user operation.

Further, when the receiving function 441 receives a user operation to start the imaging process (step S113: Yes), the imaging processing function 442 executes the imaging process in the CT imaging mode (step S114). In the present chart, the imaging processing function 442 executes only the diagnosis-purpose CT image taking process, without performing the position determining imaging process; however, it is also acceptable to perform the position determining imaging process prior to taking the diagnosis-purpose CT image.

Subsequently, the pre-processing function 445 performs the pre-processing process on the projection data 91 acquired in the imaging process in the CT imaging mode (step S115).

The reconstruction processing function 446 generates the CT image data 92 by reconstructing the pre-processed projection data 91 (step S116).

After that, the display controlling function 447 causes the display 42 to display the super resolution process operation screen 422 (step S117).

Further, the receiving function 441 judges whether or not a user operation to turn on the super resolution processing function has been received (step S118).

When the receiving function 441 receives a user operation to turn on the super resolution processing function (step S118: Yes), the super resolution processing function 444 performs the super resolution process on the CT image data 92 (step S119).

After that, the display controlling function 447 causes the display 42 to display a CT image based on the CT image data 92 resulting from the super resolution process (step S120).

On the contrary, when the receiving function 441 has not received a user operation to turn on the super resolution processing function (step S118: No) or when the receiving function 441 has received a user operation to turn off the super resolution processing function, the display controlling function 447 causes the display 42 to display a CT image based on the CT image data 92 on which the super resolution process has not been performed (step S121).

Further, the process proceeds to step S112, and when the imaging process is not to be ended, the process returns to step S101. On the contrary, when the receiving function 441 receives an operation to end the imaging process (step S112: Yes), the process in the present flowchart ends (step S112).

As explained above, the X-ray CT apparatus 1 according to the present embodiment is capable of imaging the patient P in the two types of imaging modes, namely, the X-ray fluoroscopy imaging mode and the CT imaging mode. The data subject to the super resolution process is switched depending on which mode was used for imaging the patient P between the X-ray fluoroscopy imaging mode and the CT imaging mode. Consequently, according to the present embodiment, by using the single X-ray CT apparatus 1, it is possible to perform both the imaging process to take the CT image and the imaging process to take the high-precision X-ray projection fluoroscopic image.

Imaging methods used in intervention treatment and the like during which a medical doctor implements manipulation on a patient while imaging the patient conventionally include a method by which the patient is imaged while using two apparatuses, namely, an X-ray CT apparatus and an X-ray angiography apparatus. Accordingly to this method, because both of the two apparatuses (i.e., the X-ray CT apparatus and the X-ray angiography apparatus) are required, it would be necessary to have a large examination room available. Further, because the patient would be moved between the two modalities, it might require certain time to switch between taking an X-ray projection fluoroscopic image and taking a CT image.

As another comparison example, an angio-CT apparatus is known in which an X-ray CT apparatus and an X-ray angiography apparatus are combined together. The angio-CT apparatus includes, in addition to a gantry similar to one included in a normal CT apparatus, a C-arm similar to one included in an X-ray angiography apparatus. The angio-CT apparatus, as a single apparatus, is capable of taking both an X-ray projection fluoroscopic image and a CT image; however, because the apparatus includes both the gantry and the C-arm, the apparatus is larger than normal X-ray CT apparatuses. Further, because the gantry is used for taking the CT image and the C-arm is used for taking the X-ray projection fluoroscopic image, the patient would need to be moved at the time of switching between the imaging processes.

In contrast, the X-ray CT apparatus 1 according to the present embodiment is capable of performing the two types of imaging processes while employing the single imaging system, in the X-ray fluoroscopy imaging mode to obtain the X-ray projection fluoroscopic image and in the CT imaging mode to obtain the CT image. Consequently, it is possible to save space occupied by the X-ray CT apparatus 1 and to shorten the time period required by switching between the imaging processes.

Further, generally speaking, X-ray Flat Panel Detectors (FPDs) used in X-ray angiography apparatuses have a better spatial resolution than X-ray detectors used in X-ray CT apparatuses. In an example, X-ray flat panel detectors in X-ray angiography apparatuses commonly have a spatial resolution of 0.1 mm or smaller, while ADCT apparatuses have a spatial resolution of approximately 0.3 mm. For this reason, when projection data from a normal X-ray CT apparatus is displayed as an X-ray projection fluoroscopic image, the spatial resolution may be insufficient in some situations. Further, in an endeavor to enhance spatial resolutions, it may be difficult for cost-related reasons or the like to increase the number of detecting elements in the X-ray detector of an X-ray CT apparatus to approximately match the number of detecting elements in an X-ray angiography apparatus.

In contrast, the X-ray CT apparatus 1 according to the present embodiment includes the super resolution processing function and is configured to switch between the data subject to the super resolution process depending on which mode was used for imaging the patient P between the X-ray fluoroscopy imaging mode and the CT imaging mode. Accordingly, when the X-ray fluoroscopy imaging mode is used, it is possible to generate an X-ray projection fluoroscopic image having a high spatial resolution.

More specifically, when the patient P was imaged in the X-ray fluoroscopy imaging mode, the X-ray CT apparatus 1 according to the present embodiment is configured to perform the super resolution process on the projection data 91 and to cause the display 42 to display the projection data 91 resulting from the super resolution process as an X-ray projection fluoroscopic image. Consequently, at the time of intervention treatment or the like during which a medical doctor implements manipulation on the patient P, the X-ray CT apparatus 1 according to the present embodiment is able to present the X-ray projection fluoroscopic image having a high spatial resolution by performing the super resolution process.

Further, when the patient P was imaged in the CT imaging mode, the X-ray CT apparatus 1 according to the present embodiment is configured to generate the CT image data 92 by reconstructing the projection data 91 and to further perform the super resolution process on the CT image data 92. Consequently, the X-ray CT apparatus 1 according to the present embodiment is able to enhance the spatial resolution, not only of X-ray projection fluoroscopic images, but also of normal CT images.

Further, the X-ray CT apparatus 1 according to the present embodiment is configured to control the imaging system so as to image the patient P in one of the X-ray fluoroscopy imaging mode and the CT imaging mode in accordance with a selection made by the user. Consequently, the X-ray CT apparatus 1 according to the present embodiment is able to image the patient P by using the imaging mode desired by the user.

Further, the X-ray CT apparatus 1 according to the present embodiment is configured to cause the display 42 to display the X-ray fluoroscopy imaging mode selecting button 71 capable of receiving a user operation to select the X-ray fluoroscopy imaging mode and the CT imaging mode selecting button 72 capable of receiving a user operation to select the CT imaging mode. Consequently, the X-ray CT apparatus 1 according to the present embodiment makes it possible for the user to easily select from between the imaging modes.

Further, the X-ray CT apparatus 1 according to the present embodiment is configured to perform the super resolution process when the user selects execution of the super resolution process. Consequently, when the user so desires, the X-ray CT apparatus 1 according to the present embodiment is able to generate either X-ray projection fluoroscopic image data or CT image data of which the spatial resolution is enhanced.

Further, regardless of which mode is selected by the user from between the X-ray fluoroscopy imaging mode and the CT imaging mode, the X-ray CT apparatus 1 according to the present embodiment is configured to display the super resolution process execution button 73 in mutually the same mode. Consequently, by using the X-ray CT apparatus 1 according to the present embodiment, the user is able to perform the operation to execute the super resolution process without being conscious that the data subject to the super resolution process varies depending on the imaging mode.

Second Embodiment

In the first embodiment described above, the spatial resolution of the X-ray projection fluoroscopic image is enhanced by the super resolution process. In contrast, in a second embodiment, the spatial resolution of an X-ray projection fluoroscopic image is enhanced by using a Flying Focal Spot (FFS) scheme.

Figure 8:
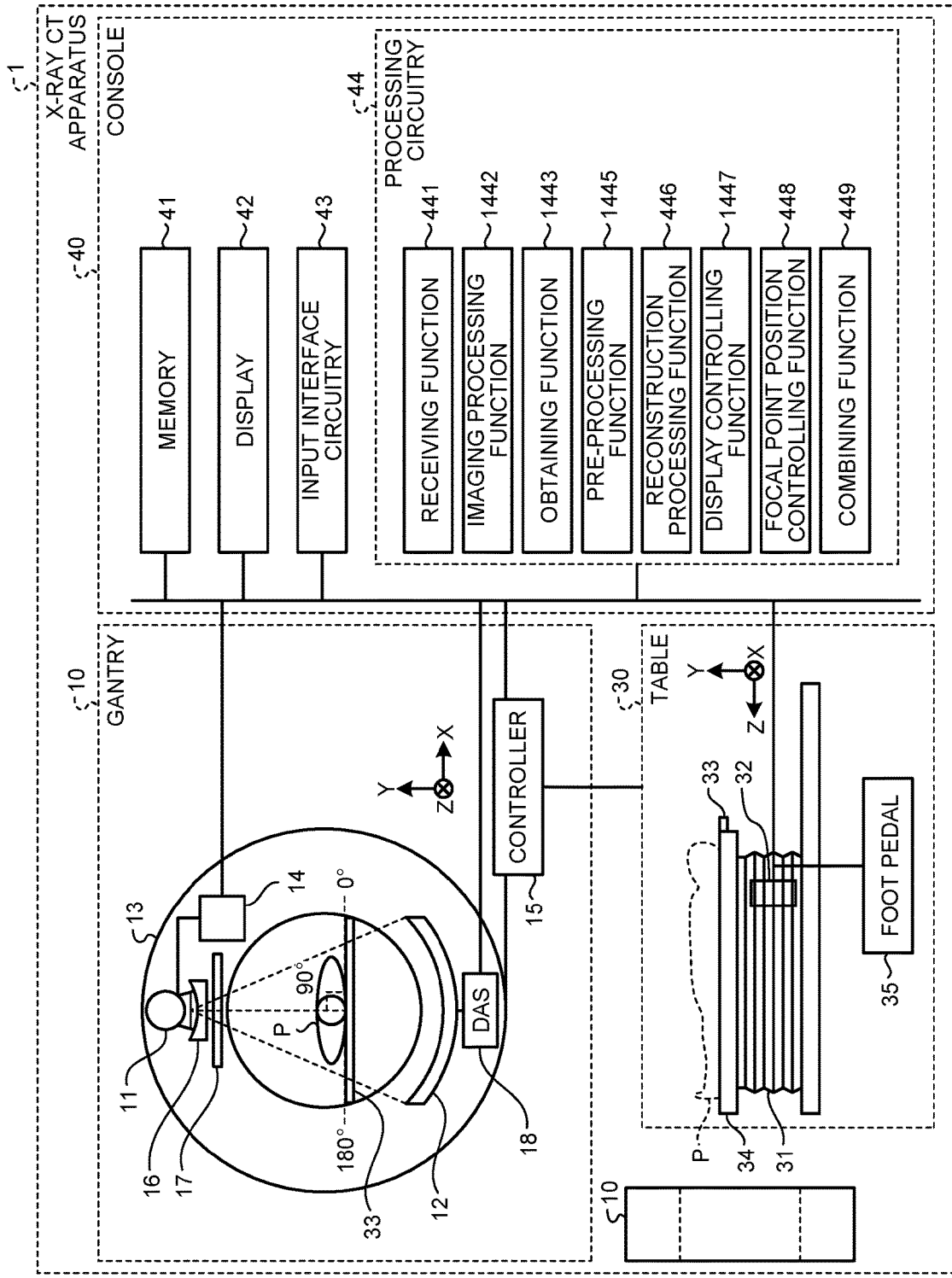
FIG. 8 is a diagram illustrating an exemplary configuration of an X-ray CT apparatus according to a second embodiment.

FIG. 8 is a diagram illustrating an exemplary configuration of the X-ray CT apparatus 1 according to the second embodiment. Similarly to the first embodiment, the X-ray CT apparatus 1 according to the present embodiment includes the gantry 10, the table 30, and the console 40. The hardware configurations of the table 30 and the console 40 are the same as those in the first embodiment.

Figure 9:
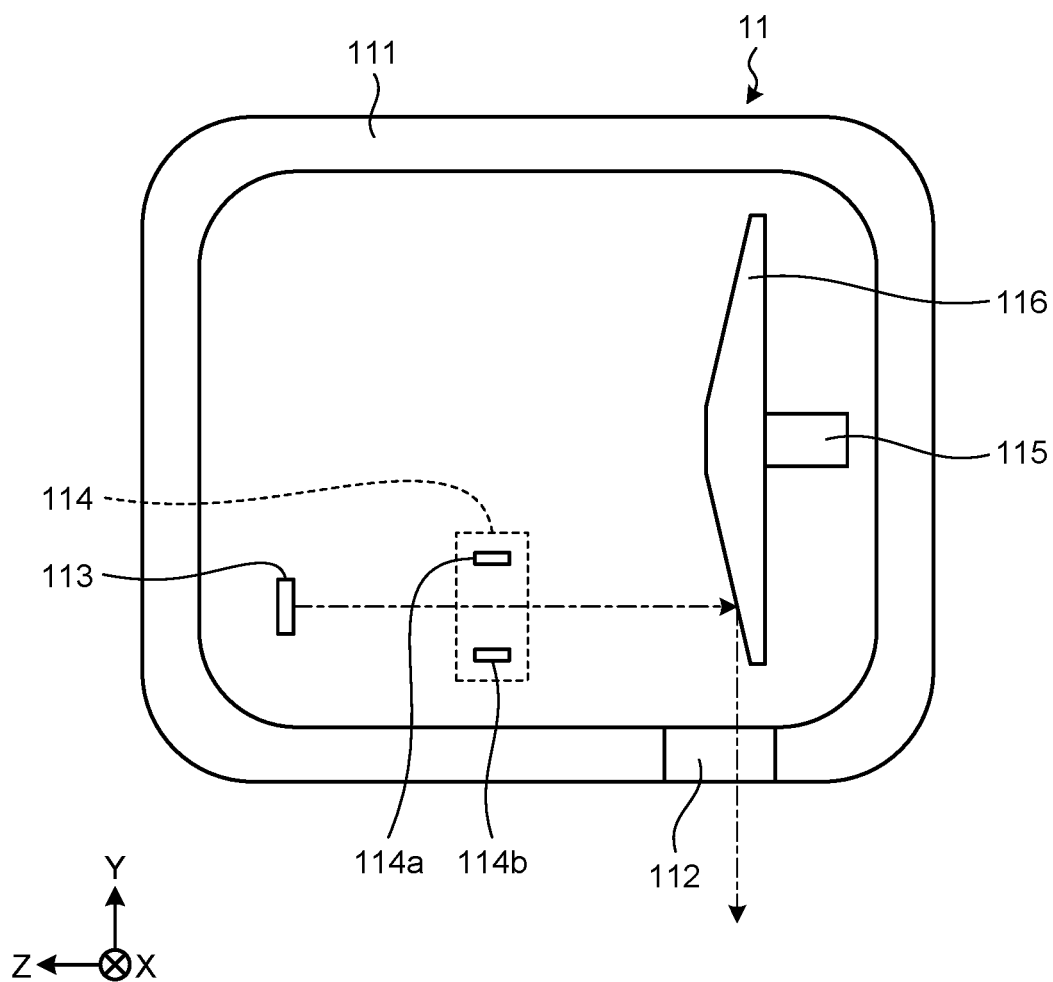
FIG. 9 is a diagram illustrating an exemplary configuration of an X-ray tube according to the second embodiment.

Further, the X-ray tube 11 according to the present embodiment includes a thermo electron adjusting unit configured to adjust a track of thermo electrons. FIG. 9 is a diagram illustrating an exemplary configuration of the X-ray tube 11 according to the second embodiment.

As illustrated in FIG. 9, the X-ray tube 11 according to the present embodiment includes a casing (an X-ray tube housing) 111, a negative pole 113, a thermo electron adjusting mechanism 114, a rotating shaft 115, and a positive pole 116. The casing 111 is manufactured by using metal, for example, and has an X-ray window 112 that passes the X-rays generated on the inside thereof. The negative pole 113 is configured to generate thermo electrons. The thermo electrons are electrons that are excited by heat generated by an electric current flowing in a filament and that jump out of the filament or a heated component part.

The positive pole 116 is configured to generate X-rays as the thermo electrons released from the negative pole 113 collide therewith. More specifically, a large potential difference is provided between the negative pole 113 and the positive pole 116. For example, the potential difference is provided between the negative pole 113 and the positive pole 116 by grounding the positive pole 116 and making the potential of the negative pole 113 negative. Due to the potential difference, the thermo electrons released from the negative pole 113 are accelerated so as to collide with the positive pole 116, and the X-rays are thus generated. Further, the positive pole 116 is a rotating body that rotates on the rotating shaft 115, and when viewed in the axial direction of the rotating shaft 115, the outer circumference thereof has a circular shape. The positive pole 116 has an umbrella-like shape, while the tip end side of the umbrella is directed toward the negative pole 113. The side of the positive pole 116 facing the negative pole 113 is a tapered face, which is formed so as to tilt toward the X-ray window 112 by a small angle with respect to the negative pole 113 side. With the rotation, the positive pole 116 is configured to distribute the positions in which heat is generated due to the collisions of the thermo electrons, so as to prevent the surface of the positive pole 116 from being melted by the generated heat. The rotating shaft 115 is supported by a bearing (not illustrated) or the like and is driven to rotate by a rotating magnetic field generated by a stator coil (not illustrated) or the like. Further, although in FIG. 9, the track (indicated with the dashed chain line) of the thermo electrons from the negative pole 113 to the positive pole 116 is depicted as running parallel to the rotation shaft 115 of the positive pole 116, possible embodiments are not limited to this example.

Under control of the processing circuitry 44, the thermo electron adjusting mechanism 114 is configured to adjust the track of the thermo electrons. More specifically, the thermo electron adjusting mechanism 114 is provided so as to sandwich the track along the track of the thermo electrons positioned between the negative pole 113 and the positive pole 116 and is configured to change the track of the thermo electrons released from the negative pole 113 by using an electric field or a magnetic field and is configured to move a focal point on the positive pole 116. The thermo electron adjusting mechanism 114 is an example of the thermo electron adjusting unit according to the present embodiment.

When the electric field is used for adjusting the track, adjustment poles 114a and 114b are each a plate-like electrode or a magnetic pole of an electromagnet, for example. In this situation, the thermo electron adjusting mechanism 114 does not necessarily have to be provided within the casing 111, and the thermo electron adjusting mechanism 114 may be provided on the outside of the casing 111. In the present embodiment, the thermo electron adjusting mechanism 114 has a function of an XYZ-FFS capable of changing a focal point position in the X-Y directions and the Z-directions. Further, the quantity and the position of the thermo electron adjusting mechanism 114 and the directions in which the focal point position is changed are not limited to the examples described above.

Returning to the description of FIG. 8, the processing circuitry 44 of the console 40 according to the present embodiment includes the receiving function 441, an imaging processing function 1442, an obtaining function 1443, a pre-processing function 1445, the reconstruction processing function 446, a display controlling function 1447, a focal point position controlling function 448, and a combining function 449. The receiving function 441 is an example of a receiving unit. The imaging processing function 1442 is an example of an imaging processing unit. The obtaining function 1443 is an example of an obtaining unit. The pre-processing function 1445 is an example of a pre-processing unit. The reconstruction processing function 446 is an example of a reconstruction processing unit. The display controlling function 1447 is an example of a display controlling unit and an output unit. The focal point position controlling function 448 is an example of a focal point position controlling unit. The combining function 449 is an example of a combining unit. The processing functions are recorded in the memory 41 in the form of computer-executable programs.

The receiving function 441 and the reconstruction processing function 446 have the same functions as those in the first embodiment.

Similarly to the first embodiment, the imaging processing function 1442 is configured to control the imaging system in the two types of imaging modes, namely, the X-ray fluoroscopy imaging mode and the CT imaging mode, so as to perform imaging processes.

Further, the imaging processing function 1442 according to the present embodiment is configured to rotate the rotating frame 13 at the time of an imaging process in the X-ray fluoroscopy imaging mode. Further, while the position of the X-ray tube 11 supported by the rotating frame 13 is within a prescribed range, the imaging processing function 1442 is configured to cause the X-ray tube 11 to emit X-rays. In other words, unlike in normal CT imaging processes, the X-ray tube 11 is configured, during an imaging process in the X-ray fluoroscopy imaging mode, to intermittently perform imaging processes only while the position of the X-ray tube 11 is in the prescribed range, instead of emitting the X-rays continuously. Details of the X-ray emission timing in the present embodiment will be explained later.

While an imaging process is performed by the imaging processing function 1442, the focal point position controlling function 448 is configured to switch the focal point position of the thermo electrons on the positive pole 116 into a plurality of mutually-different positions, by controlling the thermo electron adjusting mechanism 114. Further, in the present embodiment, the focal point position controlling function 448 is configured to the focal point position switching process at least during the imaging processes in the X-ray fluoroscopy imaging mode. Further, the focal point position controlling function 448 may also perform the focal point position switching process in the CT imaging mode.

More specifically, the focal point position controlling function 448 is configured to change the focal point position of the thermo electrons, with prescribed timing synchronized with changes, with respect to the patient P, of the positions of the X-ray tube 11 and the X-ray detector 12 provided on the rotating frame 13 that rotates during the imaging process.

Figure 10:
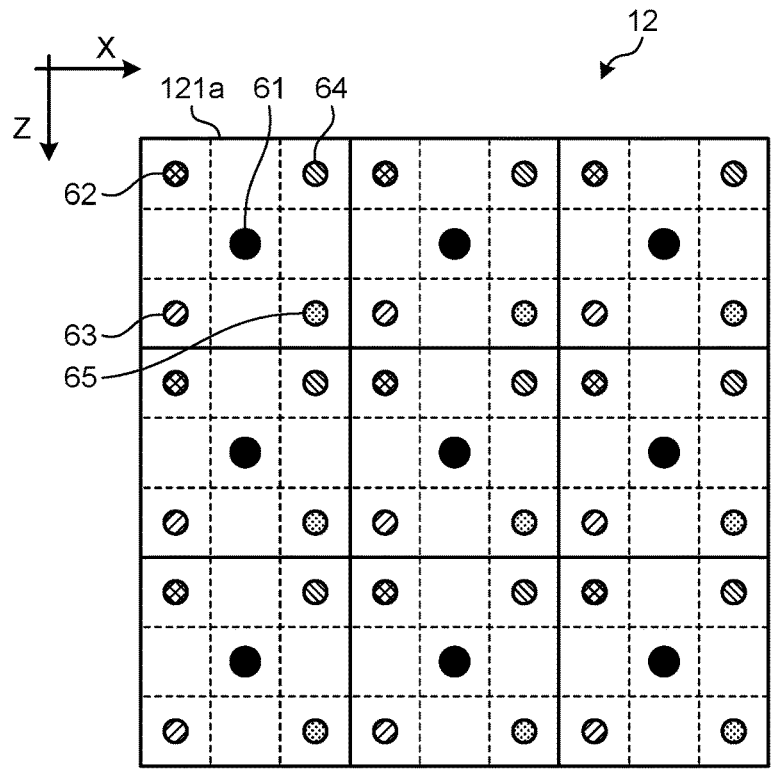
FIG. 10 is a drawing schematically illustrating an example of a plurality of focal point positions according to the second embodiment.

FIG. 10 is a drawing schematically illustrating an example of the plurality of focal point positions according to the second embodiment. FIG. 10 illustrates center positions 61 to 65 observed when X-rays having mutually-different focal point positions are emitted from the X-ray tube 11 onto the plurality of detecting elements of the X-ray detector 12.

For example, the center position 61 illustrated in FIG. 10 is a center position of the X-rays in the situation where X-rays are emitted from the X-ray tube 11 onto the X-ray detector 12 while the focal point position is in a reference position. The reference position is a default focal point position observed when the thermo electron adjusting mechanism 114 has not changed the focal point position.

Further, the center positions 62 to 65 of the X-rays are each a center position of the X-rays emitted onto a detecting element 121a, in the situation where the thermo electron adjusting mechanism 114 has moved the focal point position from the reference position in the X-Y direction or the Z-direction. The movement in the X-Y direction is a movement of the focal point position on an X-Y plane defined with an X-direction and a Y-direction. The X-Y direction may be referred to as a fan direction. Further, the movement in the Z-direction is a movement of the focal point position along the body axis direction of the patient P.

Further, although FIG. 10 uses the example of the single detecting element 121a among the plurality of detecting elements included in the X-ray detector 12, the center position of the emitted X-rays similarly changes for the other detecting elements as well, according to changes of the focal point position.

As explained above, because the X-rays are emitted with the plurality of focal point positions, oversampling acquisition becomes possible. Thus, even if the number of detecting elements is unchanged, it is possible to enhance the spatial resolution of the X-ray CT apparatus 1.

Figure 11:
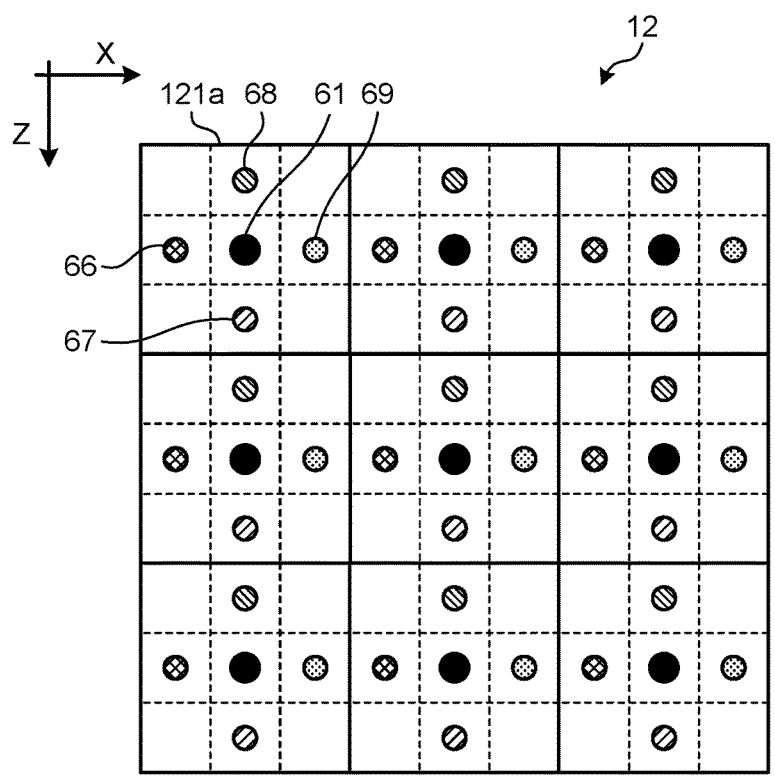
FIG. 11 is a drawing schematically illustrating another example of a plurality of focal point positions according to the second embodiment.

Further, the quantity and the positions of the focal point position are not limited to the example illustrated in FIG. 10. FIG. 11 is a drawing schematically illustrating another example of a plurality of focal point positions according to the second embodiment. For example, center positions 66 to 69 of the X-rays may be positioned as illustrated in FIG. 11, as a result of the moving of the focal point.

Next, changes of the focal point position and X-ray emission timing will be explained.

Figure 12:
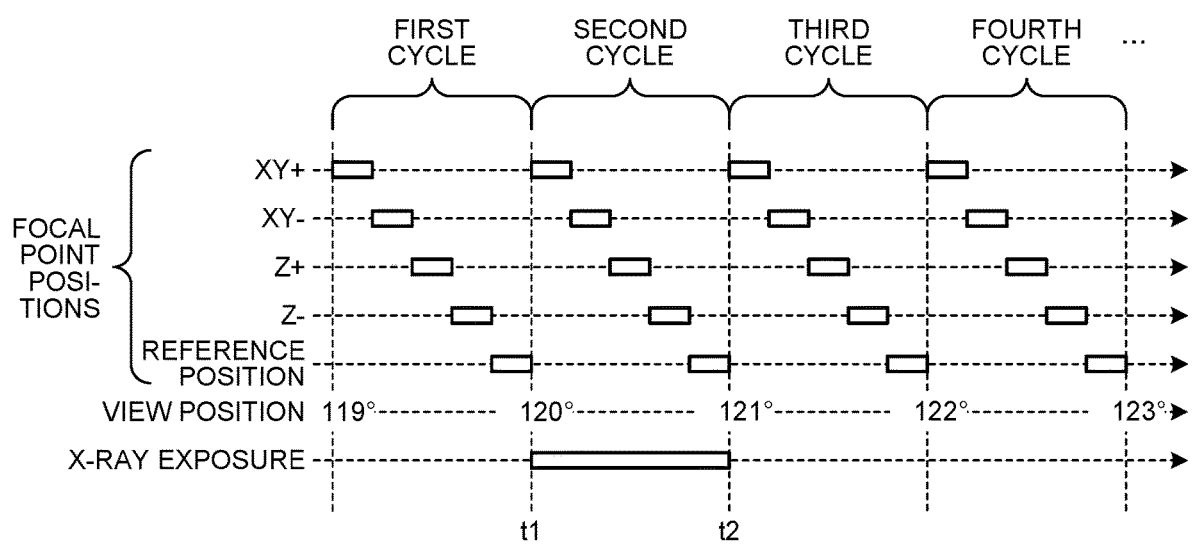
FIG. 12 is a drawing illustrating an example of X-ray emission timing according to the second embodiment.

FIG. 12 is a drawing illustrating an example of X-ray emission timing according to the second embodiment. While using a set in which a plurality of focal point positions are defined in prescribed order and in a prescribed quantity as one cycle, the focal point position controlling function 448 is configured to repeat switching of the focal point position as many times as a plurality of cycles. Although FIG. 12 illustrates the first to the fourth cycles, possible number of cycles are not limited to this example.

In the example in FIG. 12, the focal point position controlling function 448 uses five focal point positions, namely, "XY+", "XY−", "Z+", "Z−", and the "reference position", as one cycle.

The position "XY+" denotes a focal point position resulting from moving from the "reference position" in an X-Y direction. The position "XY−" denotes a focal point position resulting from moving from the "reference position" in another X-Y direction different from that of "XY+". The position "Z+" denotes a focal point position resulting from moving from the "reference position" in a Z-direction. The position "Z−" denotes a focal point position resulting from moving from the "reference position" in another Z-direction different from that of "Z+". In the example in FIG. 12, the prescribed order is defined as follows: "XY+", "XY−", "Z+", "Z−", and the "reference position". More specifically, among the five focal point positions included in one cycle, "XY+" is the first focal point position; "XY−" is the second focal point position; "Z+" is the third focal point position; "Z−" is the fourth focal point position; and the "reference position", is the last focal point position.

In the example in FIG. 12, because the rotating frame 13 is rotating, the position of the X-ray tube 11 (i.e., the view position) changes. It is assumed that the time period in which the view position moves by one degree is synchronized with the time period of one cycle of the focal point position. More specifically, as illustrated in FIG. 12, when the view position is at 119°, the focal point position is at "XY+", which is the beginning of one cycle. When the view position is at 120°, the focal point position is again at "XY+", which is the beginning of one cycle. In other words, in the time period during which the view position moves by one degree, the focal point position controlling function 448 changes the focal point position by an amount corresponding to one cycle. However, the moving speed of the focal point position and the timing are not limited to those in this example.

In FIG. 12, "X-ray exposure" denotes timing with which X-rays are emitted from the X-ray tube 11 under control of the imaging processing function 1442. In the example in FIG. 12, during the movement of the view position by one degree from 120° to 121°, X-rays are emitted by the X-ray tube 11. The range of the view position from 120° to 121° corresponds to an example of the prescribed range of the position of the X-ray tube 11 according to the present embodiment.

The time t1 in FIG. 12 is an X-ray emission start time, whereas the time t2 is an X-ray emission end time. As for the view position at which the X-rays are emitted, an appropriate angle may be set by the user to acquire an X-ray projection fluoroscopic image of the patient P or the position may be determined in advance. The time t1 and the time t2 are each an example of the prescribed timing synchronized with the view position. In the present embodiment, the X-ray emission start time and emission end time are determined by the view position.

Although FIG. 12 illustrates an example in which the time period during which the view position moves by one degree (i.e., the time period from the beginning to the end in each cycle of the moving cycles of the focal point position) is used as the X-ray emission period, possible lengths of the X-ray emission period are not limited to this example. For instance, the time period during which the view position moves by two degrees may be an X-ray emission period.

Because the X-rays are emitted only while the position of the X-ray tube 11 is within the prescribed range, it is possible to reduce the amount of emitted X-rays, compared to the situation where X-rays are continuously emitted regardless of the view position.

Returning to the description of FIG. 8, while X-rays are emitted, the obtaining function 1443 is configured to obtain the projection data 91 from the DAS 18 with respect to each of the focal point positions. In the present embodiment, because there are five focal point position switching processes in one cycle, the obtaining function 1443 is configured to obtain five pieces of projection data 91, every time the view point changes by one degree.

The pre-processing function 1445 has the same functions as those in the first embodiment and is further configured to perform a pre-processing process on each of the plurality of pieces of projection data 91 obtained by the obtaining function 1443.

When an imaging process is executed in the X-ray fluoroscopy imaging mode, the combining function 449 is configured to generate combined projection data by combining together the plurality of pieces of projection data 91 obtained by projecting images of the patient P while using the X-rays emitted with the plurality of mutually-different focal point positions. In the present embodiment, the combining function 449 is configured to generate the combined projection data by combining together all the pieces of projection data 91 obtained by projecting images of the patient P from the start to the end of the X-ray emission.

More specifically, the combining function 449 according to the present embodiment is configured to make one piece of combined projection data from the plurality of pieces of projection data 91 on which the pre-processing process has been performed by the pre-processing function 1445. In this situation, it is acceptable to adopt a publicly-known technique as a method for combining together the plurality of pieces of projection data 91.

The display controlling function 1447 has the same functions as those in the first embodiment and is further configured to cause the display 42 to display the combined projection data as an X-ray projection fluoroscopic image.

Next, a flow in an imaging process performed by the X-ray CT apparatus 1 according to the present embodiment configured as described above will be explained.

Figure 13:
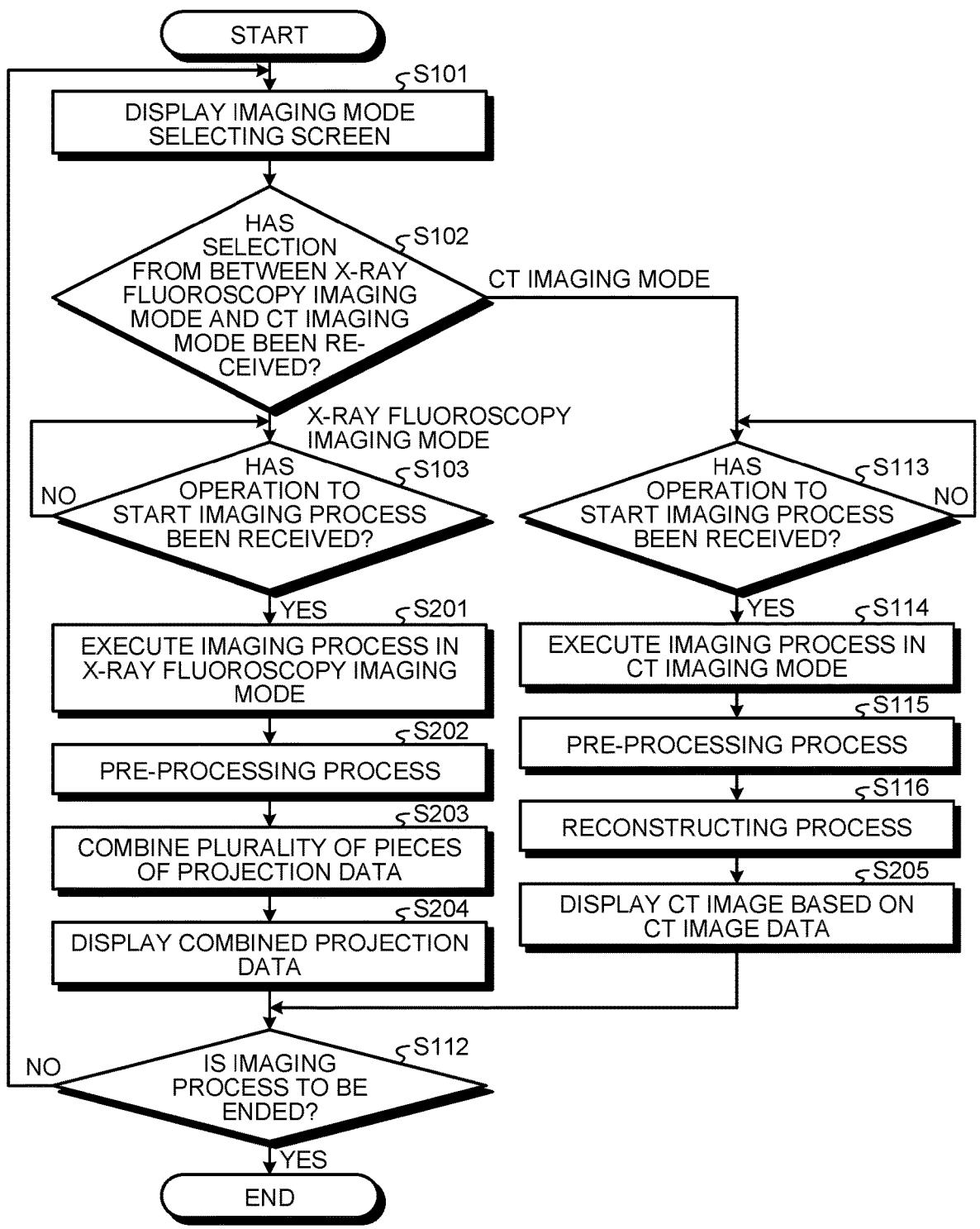
FIG. 13 is a flowchart illustrating an example of a flow in an imaging process performed by the X-ray CT apparatus according to the second embodiment.

FIG. 13 is a flowchart illustrating an example of a flow in the imaging process performed by the X-ray CT apparatus 1 according to the second embodiment.

The processes from step S101 at which the imaging mode selecting screen 421 is displayed through step S103 at which a user operation to start the imaging process is received are the same as those in the first embodiment.

While the X-ray fluoroscopy imaging mode is selected by the user, when the receiving function 441 receives a user operation to start an imaging process (step S103: Yes), the imaging processing function 1442 executes the imaging process in the X-ray fluoroscopy imaging mode (step S201). In the present embodiment, at the time of the imaging process in the X-ray fluoroscopy imaging mode, the imaging processing function 1442 rotates the rotating frame 13 and causes the X-ray emission from the X-ray tube 11 to start and end with timing synchronized with changes of the view position of the X-ray tube 11 which occur in conjunction with the rotation of the rotating frame 13. Further, by controlling the thermo electron adjusting mechanism 114 while the imaging process is executed by the imaging processing function 1442, the focal point position controlling function 448 changes the focal point position with timing synchronized with the changes of the view position. The X-ray detector 12 is configured to acquire a plurality of pieces of projection data 91 that are oversampled by using the FFS scheme in this manner. The DAS 18 is configured to transmit the plurality of pieces of projection data 91 acquired by the X-ray detector 12 to the console 40. The obtaining function 1443 is configured to obtain the plurality of pieces of projection data 91 transmitted thereto from the DAS 18.

Subsequently, the pre-processing function 1445 performs a pre-processing process on each of the plurality of pieces of projection data 91 obtained by the obtaining function 1443 (step S202).

After that, the combining function 449 generates combined projection data by combining together the pre-processed plurality of pieces of projection data 91 (step S203).

After that, the display controlling function 1447 causes the display 42 to display the combined projection data as an X-ray projection fluoroscopic image (step S204).

Further, when the CT imaging mode is selected by the user at step S102, the processes from step S113 at which an operation to start the imaging process is received through step S116 at which the reconstructing process is performed are the same as those in the first embodiment.

After that, the display controlling function 1447 causes the display 42 to display a CT image based on the CT image data 92 (step S205).

The process at step S112 to judge whether or not the imaging process is to be ended is the same as the process in the first embodiment.

As explained above, the X-ray CT apparatus 1 according to the present embodiment is configured to generate the combined projection data by switching, while the imaging process is executed, the focal point position of the X-rays into the plurality of mutually-different positions and further combining together the plurality of pieces of projection data 91 obtained by projecting the images of the patient P by using the X-rays emitted with the plurality of mutually-different focal point positions and is configured to cause the display 42 to display the combined projection data as the X-ray projection fluoroscopic image. Consequently, in addition to the advantageous effects of the first embodiment, the X-ray CT apparatus 1 according to the present embodiment is able to generate a high-precision X-ray projection fluoroscopic image from the projection data 91 that is oversampled while using the plurality of focal point positions.

Further, the X-ray CT apparatus 1 according to the present embodiment is configured to rotate the rotating frame 13 during the imaging process so as to cause the X-ray tube 11 to emit the X-rays while the position of the X-ray tube 11 supported by the rotating frame 13 is in the prescribed range. Consequently, by employing the imaging processing function 1442, it is possible to reduce the amount of emitted X-rays, compared to the situation where X-rays are continuously emitted.

Further, the X-ray CT apparatus 1 according to the present embodiment is configured to change the focal point position of the X-rays, with the prescribed timing synchronized with the changes, with respect to the patient P, of the positions of the X-ray tube 11 and the X-ray detector 12 provided on the rotating frame 13 that rotates. Consequently, by employing the imaging processing function 1442, it is possible to change the focal point position of the X-rays by using a cycle suitable for the imaging process of the X-ray projection fluoroscopic image.

Furthermore, the X-ray CT apparatus 1 according to the present embodiment is configured to generate the combined projection data, by combining together all the pieces of projection data 91 obtained by projecting the images of the patient P from the start to the end of the X-ray emission. The display controlling function 447 is configured to cause the display 42 to display the combined projection data. Consequently, the X-ray CT apparatus 1 according to the present embodiment is able to enhance the spatial resolution of the X-ray projection fluoroscopic image, compared to the situation where projection data 91 imaged with a single focal point position is displayed as an X-ray projection fluoroscopic image.

Third Embodiment

In the second embodiment described above, the X-ray emission timing is determined on the basis of the view position. In a third embodiment, X-ray emission timing is determined in accordance with a user operation.

The hardware configuration of the X-ray CT apparatus 1 according to the present embodiment is the same as that in the second embodiment explained with reference to FIGS. 8 and 9.

Further, the processing circuitry 44 of the console 40 according to the present embodiment includes, similarly to the second embodiment, the receiving function 441, the imaging processing function 1442, the obtaining function 1443, the pre-processing function 1445, the reconstruction processing function 446, the display controlling function 1447, the focal point position controlling function 448, and the combining function 449. The receiving function 441 is an example of a receiving unit. The imaging processing function 1442 is an example of an imaging processing unit. The obtaining function 1443 is an example of an obtaining unit. The pre-processing function 1445 is an example of a pre-processing unit. The reconstruction processing function 446 is an example of a reconstruction processing unit. The display controlling function 1447 is an example of a display controlling unit and an output unit. The focal point position controlling function 448 is an example of a focal point position controlling unit.

The obtaining function 1443, the pre-processing function 1445, the reconstruction processing function 446, the display controlling function 1447, and the combining function 449 have the same functions as those in the second embodiment.

The receiving function 441 according to the present embodiment has the same functions as those in the second embodiment and is further configured to receive user operations to start and end the X-ray emission. For example, when the user steps on the foot pedal 35, the receiving function 441 is configured to receive the user operation to start the X-ray emission. Further, when the user keeps stepping on the foot pedal 35, the receiving function 441 is configured to continuously receive the user instruction to have the X-rays emitted. Further, when the user stops stepping on the foot pedal 35, the receiving function 441 is configured to receive the user operation to end the X-ray emission. In this situation, the foot pedal 35 is an example of an operating unit. It is also acceptable to use an operating button, a touch panel, and/or the like. The operation to start the X-ray emission and the operation to end the X-ray emission may be separate operations.

The imaging processing function 1442 according to the present embodiment has the same functions as those in the second embodiment and is further configured to cause the X-ray tube 11 to emit the X-rays in accordance with the timing with which the user operation to start the X-ray emission is received.

Figure 14:
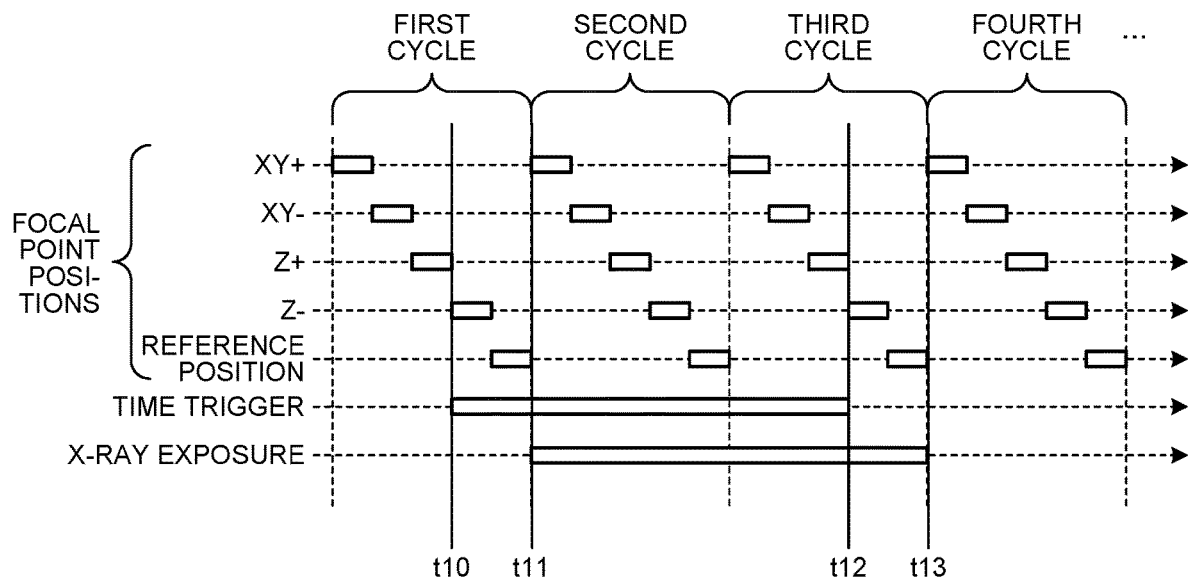
FIG. 14 is a drawing illustrating an example of X-ray emission timing according to a third embodiment.

FIG. 14 is a drawing illustrating an example of the X-ray emission timing according to the third embodiment. In FIG. 14, "Time trigger" indicates timing of a user operation for the X-ray emission. In the example in FIG. 14, the user starts stepping on the foot pedal 35 at a time t10, and the user takes his/her foot off the foot pedal 35 at a time t12. In the time period from the time t10 to the time t12, the user keeps stepping on the foot pedal 35. Although illustration of changes of the view position is omitted from FIG. 14, it is assumed in the present embodiment also that the rotating frame 13 is rotating.

Further, the focal point position controlling function 448 according to the present embodiment has the same functions as those in the second embodiment. As illustrated in FIG. 14, similarly to the second embodiment, while using a set in which a plurality of focal point positions are defined in prescribed order and in a prescribed quantity as one cycle, the focal point position controlling function 448 is configured to repeat the switching of the focal point position as many times as a plurality of cycles.

The imaging processing function 1442 according to the present embodiment is configured to cause the X-ray tube 11 to start emitting X-rays at the time when the X-ray focal point position is positioned for the first time at "XY+", which is the first focal point position in the cycle, since the user performed the operation to start the X-ray emission. In the example in FIG. 14, after the time t10 at which the user operation for the X-ray emission is received, the focal point position is positioned for the first time at "XY+" at a time t11. Consequently, the imaging processing function 1442 causes the X-ray tube 11 to start emitting the X-rays at the time t11.

Further, while the receiving function 441 is continuously receiving the user operation to start the X-ray emission, the imaging processing function 1442 causes the X-ray tube 11 to continue to emit the X-rays. In the example in FIG. 14, the imaging processing function 1442 causes the X-ray tube 11 to continue to emit the X-rays at least until the time t12.

After that, when the user operation to start the X-ray emission ends, the imaging processing function 1442 is configured to cause the X-ray tube 11 to end the X-ray emission at the time when the X-ray focal point position changes from the last focal point position in the current cycle to the first focal point position in the next cycle. In the example in FIG. 14, after the time t12 at which the user takes his/her foot off the foot pedal 35, the cycles switch for the first time at a time t13. Accordingly, the imaging processing function 1442 causes the X-ray tube 11 to end the X-ray emission at the time t13.

Next, a flow in an imaging process performed by the X-ray CT apparatus 1 according to the present embodiment configured as described above will be explained.

Figure 15:
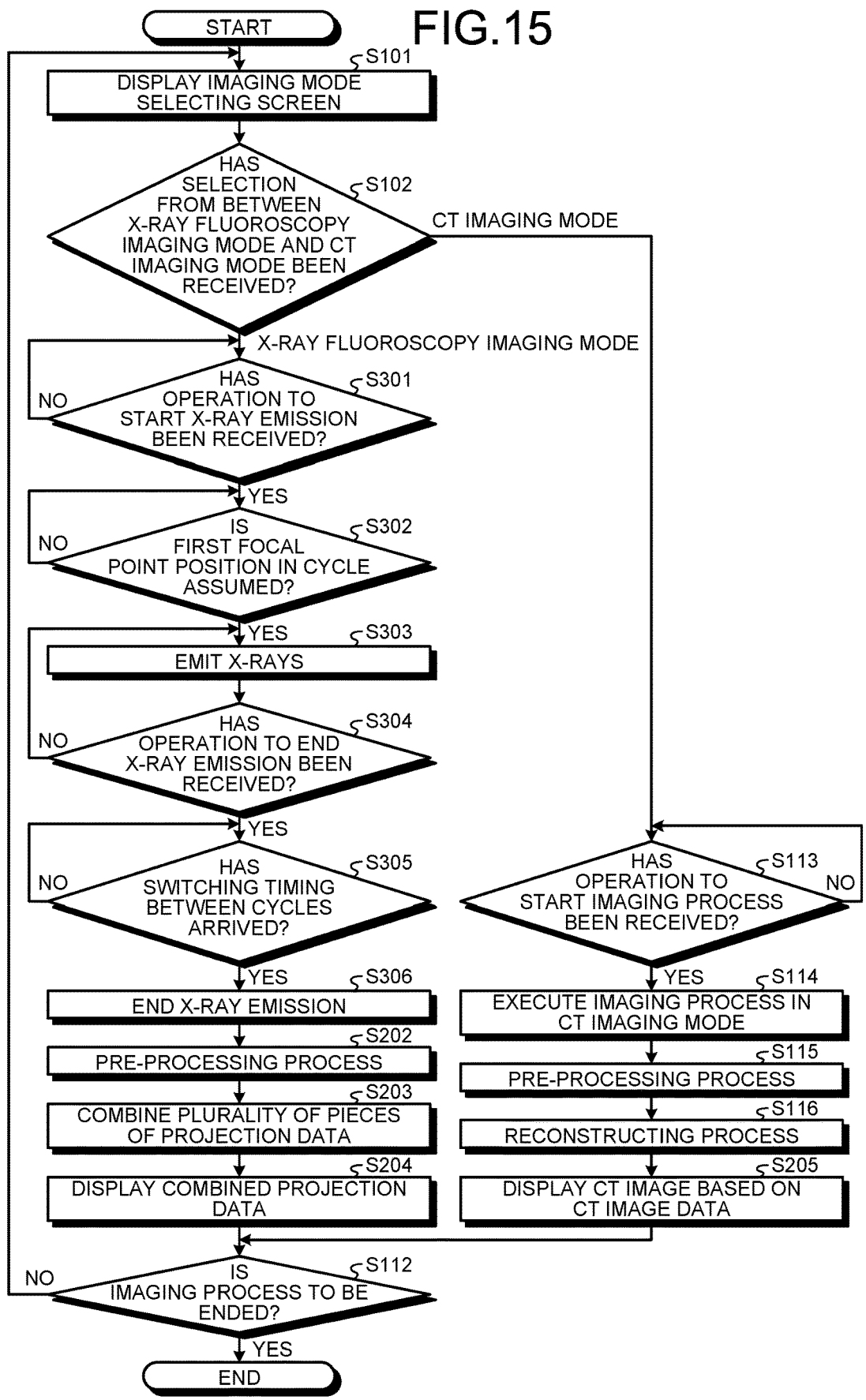
FIG. 15 is a flowchart illustrating an example of a flow in an imaging process performed by an X-ray CT apparatus according to the third embodiment.

FIG. 15 is a flowchart illustrating an example of the flow in the imaging process performed by the X-ray CT apparatus 1 according to the third embodiment.

The processes from step S101 at which the imaging mode selecting screen 421 is displayed through step S102 at which a user operation to select an imaging mode is received are the same as those in the first embodiment.

After that, when the X-ray fluoroscopy imaging mode is selected, the receiving function 441 according to the present embodiment stands by until a user operation to start the X-ray emission is received (step S301: No).

When the receiving function 441 receives a user operation to start the X-ray emission (step S301: Yes), when the X-ray focal point position comes to the first focal point position among the plurality of focal point positions included in one cycle after the operation is received (step S302: Yes), the imaging processing function 1442 according to the present embodiment causes the X-ray tube 11 to emit X-rays (step S303). For example, in the example in FIG. 14, the imaging processing function 1442 starts the X-ray emission at the time when the X-ray focal point position is positioned for the first time at "XY+" since the user performed the operation to start the X-ray emission.

Further, after the receiving function 441 receives the user operation to start the X-ray emission, until the X-ray focal point position reaches the first focal point position among the plurality of focal point positions included in the one cycle, the imaging processing function 1442 stands by without causing the X-ray tube 11 to emit X-rays (step S302: No). For instance, in the example in FIG. 14, the imaging processing function 1442 stands by without causing the X-rays to be emitted until the X-ray focal point position reaches "XY+" after the user performs the operation to start the X-ray emission.

Further, the receiving function 441 judges whether or not an operation to end the X-ray emission has been received (Step S304). For example, when the user keeps stepping on the foot pedal 35, the receiving function 441 determines that the operation to end the X-ray emission has not been received (step S304: No). In this situation, the imaging processing function 1442 causes the X-ray tube 11 to continue to emit the X-rays.

For example, when the user takes his/her foot off the foot pedal 35, the receiving function 441 determines that a user operation to end the X-ray emission is received (step S304: Yes). In this situation, the imaging processing function 1442 stands by while continuing to have the X-ray emitted, until the next switching timing of the focal point position cycle arrives (step S305: No).

Further, when the first cycle switching timing after the receipt of the user operation to end the X-ray emission arrives (step S305: Yes), the imaging processing function 1442 causes the X-ray tube 11 to end the X-ray emission (step S306).

The processes from step S202 at which the pre-processing process is performed through step S204 at which the display 42 is caused to display the combined projection data as an X-ray projection fluoroscopic image are the same as those in the first embodiment.

Further, when the user selects the CT imaging mode at step S102, the processes from step S113 at which the operation to start the imaging process is received through step S116 at which the reconstructing process is performed are the same as those in the first and the second embodiments. Further, the process at step S112 to judge whether or not the imaging process is to be ended is the same as the process in the first and the second embodiments.

As explained above, the X-ray CT apparatus 1 according to the present embodiment is configured to cause the X-ray tube 11 to emit the X-rays in accordance with the timing with which the user operation to start the X-ray emission is received. Consequently, in addition to the same advantageous effects as those of the first and the second embodiments, the X-ray CT apparatus 1 according to the present embodiment is able to acquire the X-ray projection fluoroscopic image with the timing desired by the user.

Further, the X-ray CT apparatus 1 according to the present embodiment is configured to cause the X-ray tube 11 to start emitting the X-rays at the time when the X-ray focal point position is positioned for the first time at "XY+", which is the first focal point position in the cycle, since the user performed the operation to start the X-ray emission. Consequently, by using the X-ray CT apparatus 1 according to the present embodiment, the user is able to cause the X-ray emission to be started with the timing synchronized with the cycle of the changes of the focal point position, without the need to be conscious about the cycle of the focal point position.

Furthermore, when the user operation to start the X-ray emission is ended, the X-ray CT apparatus 1 according to the present embodiment causes the X-ray emission to end, at the time when the X-ray focal point position switches from the last focal point position in the current cycle to the first focal point position in the next cycle. Consequently, by using the X-ray CT apparatus 1 according to the present embodiment, the user is able to end the X-ray emission with the timing synchronized with the cycle of the changes of the focal point position, without the need to be conscious about the cycle of the focal point position.

Fourth Embodiment

In the third embodiment described above, at the time of the imaging process in the X-ray fluoroscopy imaging mode, the X-ray emission timing is determined in accordance with the timing of the user operation and the switching timing of the cycles corresponding to the sets each made up of the plurality of focal point positions. In a fourth embodiment, timing of X-ray emission is determined in accordance with timing of a user operation and timing of switching in units of focal point positions, regardless of the timing of the switching between the cycles.

The hardware configuration of the X-ray CT apparatus 1 according to the present embodiment is the same as that in the second and the third embodiments.

Further, similarly to the second and the third embodiments, the processing circuitry 44 of the console 40 according to the present embodiment includes the receiving function 441, the imaging processing function 1442, the obtaining function 1443, the pre-processing function 1445, the reconstruction processing function 446, the display controlling function 1447, the focal point position controlling function 448, and the combining function 449. The receiving function 441 is an example of a receiving unit. The imaging processing function 1442 is an example of an imaging processing unit. The obtaining function 1443 is an example of an obtaining unit. The pre-processing function 1445 is an example of a pre-processing unit. The reconstruction processing function 446 is an example of a reconstruction processing unit. The display controlling function 1447 is an example of a display controlling unit and an output unit. The focal point position controlling function 448 is an example of a focal point position controlling unit.

The obtaining function 1443, the pre-processing function 1445, the reconstruction processing function 446, the display controlling function 1447, and the focal point position controlling function 448 have the same functions as those in the second embodiment.

The imaging processing function 1442 according to the present embodiment is configured to cause the X-ray tube 11 to start emitting X-rays at the time when the X-ray focal point position switches for the first time since the X-ray tube 11 becomes able to emit X-rays after the user operation to start the X-ray emission.

Figure 16:
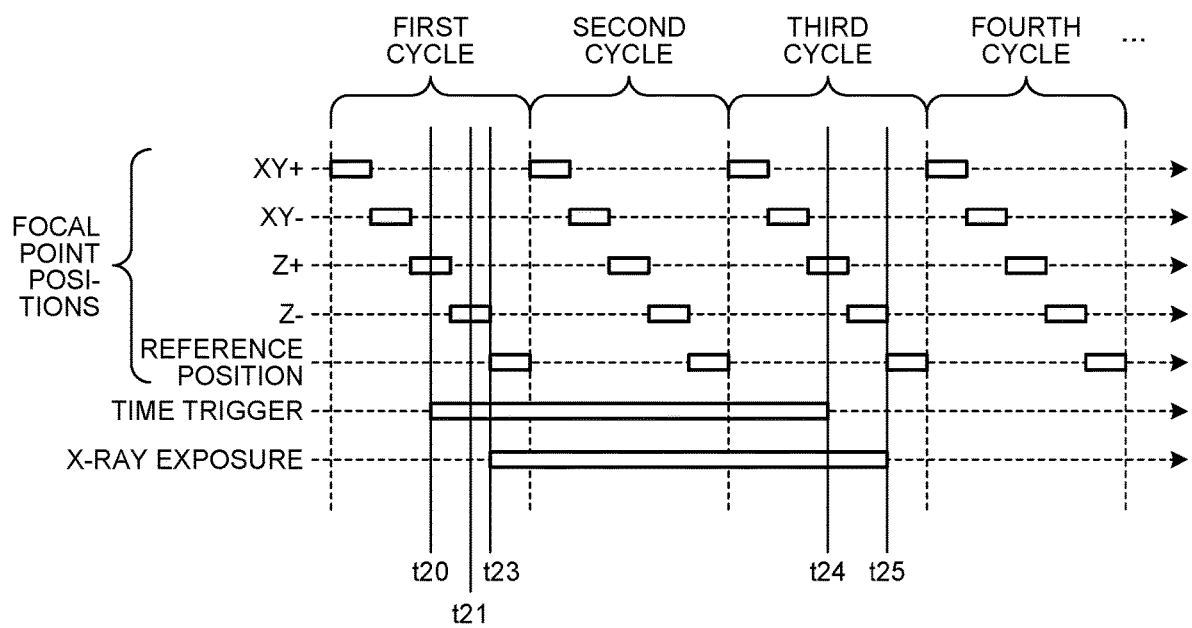
FIG. 16 is a drawing illustrating an example of X-ray emission timing according to a fourth embodiment.

FIG. 16 is a drawing illustrating an example of the X-ray emission timing according to the fourth embodiment. As illustrated in FIG. 16, in the present embodiment, the X-ray emission can start or end even during a cycle, regardless of the switching timing of the cycles corresponding to sets each made up of a plurality of focal point distances.

For instance, in the example in FIG. 16, at a time t20, the user performs an operation to instruct that the X-ray emission be started by stepping on the foot pedal 35 or the like. After that, the user takes his/her foot off the foot pedal 35 at a time t24.

There may be a time lag between when the user performs the operation to instruct that the X-ray emission be started and when the X-ray tube 11 becomes able to emit the X-rays. In the example in FIG. 16, let us assume that, after the time t20 at which the user performs the operation to instruct that the X-ray emission be started, the X-ray tube 11 becomes able to emit the X-rays at a time t21. However, the time t21 does not coincide with the switching timing of the focal point position. In this situation, the time at which the X-ray focal point position switches for the first time since the X-ray tube 11 becomes able to emit the X-rays after the user operation to start the X-ray emission is a time t23. Consequently, at the time t23 when the focal point position switches from "Z−" to the "reference position", the imaging processing function 1442 causes the X-ray tube 11 to start emitting the X-rays.

Further, the imaging processing function 1442 is configured to cause the X-ray tube 11 to end emitting the X-rays at the time when the X-ray focal point position switches for the first time since the user performed the operation to end the X-ray emission. Similarly to the third embodiment, the user operation to end the X-ray emission is a user operation to take his/her foot off the foot pedal 35, for example. The time at which the X-ray focal point position switches for the first time since a time t24 at which the user takes his/her foot off the foot pedal 35 is a time t25. Accordingly, the imaging processing function 1442 causes the X-ray tube 11 to end the X-ray emission at the time t25.

The combining function 449 according to the present embodiment has the same functions as those in the second and the third embodiments and is further configured, when the X-ray emission period of the X-ray tube 11 extends over multiple cycles, to combine a plurality of pieces of projection data 91 generated by the X-rays emitted with the focal point positions corresponding to the X-ray emission period among the plurality of focal point positions included in the cycles.

More specifically, when the X-ray emission period starts at a time during a first cycle of the X-ray focal point position and ends at a time during a second cycle, the combining function 449 is configured to generate combined projection data by combining together the plurality of consecutive pieces of projection data 91, starting with a piece of projection data 91 corresponding to the first focal point position in the X-ray emission period among a plurality of focal point positions included in the first cycle and ending with a piece of projection data 91 corresponding to the last focal point position in the X-ray emission period among a plurality of focal point positions included in the second cycle. In this situation, the first cycle and the second cycle serve as examples of a plurality of consecutive cycles and are not meant to limit the quantity of the cycles.

In the example in FIG. 16, the X-ray emission period lasts from the last focal point position (the "reference position") in the first cycle to the fourth focal point position "Z−" in the third cycle. In this situation, the combining function 449 is configured to generate the combined projection data by combining together ten pieces of projection data 91 in total corresponding to the last focal point position (the "reference position") in the first cycle, the first to the last focal point positions in the second cycle, and the first to the fourth focal point positions in the third cycle.

As explained above, the X-ray CT apparatus 1 according to the present embodiment causes the X-ray tube 11 to start emitting the X-rays, at the time when the X-ray focal point position switches for the first time since the X-ray tube 11 becomes able to emit the X-rays after the user operation to start the X-ray emission. Consequently, in addition to the advantageous effects of the second and the third embodiments, the X-ray CT apparatus 1 according to the present embodiment is able to change the X-ray emission period, regardless of the switching timing of the cycles corresponding to the sets each made up of the plurality of focal point positions. It is therefore possible to enhance the degree of freedom of the user regarding the X-ray emission period.

First Modification Example

The first embodiment described above may be combined with the second to the fourth embodiments. For example, the X-ray CT apparatus 1 according to the first embodiment may have the FFS function similarly to the X-ray CT apparatus 1 according to any of the second to the fourth embodiments. More specifically, similarly to the X-ray CT apparatus 1 according to any of the second to the fourth embodiments, the X-ray CT apparatus 1 according to the first embodiment may include the thermo electron adjusting mechanism 114, the focal point position controlling function 448 configured to control the thermo electron adjusting mechanism 114, and the combining function 449 configured to combine together a plurality of pieces of projection data 91. The super resolution processing function 444 according to the present modification example is configured to perform the super resolution process on the combined projection data. In that situation, the display controlling function 447 or 1447 is configured to cause the display 42 to display the combined projection data resulting from the super resolution process.

The X-ray CT apparatus 1 according to the present modification example is configured to perform the super resolution process on the combined projection data obtained by combining together the plurality of pieces of projection data 91 corresponding to the mutually-different focal point positions. It is therefore possible to further enhance the resolution of the X-ray projection fluoroscopic image.

Second Modification Example

In the fourth embodiment described above, when the X-ray emission period starts at a time during the first cycle of the X-ray focal point position and ends at a time during the second cycle, the combining function 449 is configured to combine the pieces of projection data 91 acquired during the X-ray emission period, without distinguishing the first cycle from the second cycle; however, possible methods for combining pieces of projection data 91 when the X-ray emission period extends over multiple cycles are not limited to the method described above.

For example, when the X-ray emission period extends over multiple cycles, the combining function 449 may perform the combining process at stages, by combining pieces of projection data 91 for each of the cycles and further combining pieces of combined projection data together.

More specifically, when the X-ray emission period of the X-ray tube 11 starts at a time during the first cycle of the X-ray focal point position and ends at a time during the second cycle, the combining function 449 is configured to generate first combined projection data by combining together one or more pieces of projection data 91 corresponding to one or more focal point positions falling in the X-ray emission period among the plurality of focal point positions included in the first cycle. Further, the combining function 449 is configured to generate second combined projection data by combining together one or more pieces of projection data corresponding to one or more focal point positions falling in the X-ray emission period among the plurality of focal point positions included in the second cycle. After that, the combining function 449 is configured to generate third combined projection data by combining the first combined data with the second combined data.

The display controlling function 1447 according to the present modification example is configured to cause the display 42 to display the third combined projection data as an X-ray projection fluoroscopic image.

With the image processing process performed at stages in this manner, it is possible to improve efficiency of the process by, for example, starting to combine pieces of projection data 91 corresponding to the cycle that ended earlier, before the X-ray emission period ends.

Third Modification Example

In the embodiments described above, the example was explained in which the X-ray projection fluoroscopic image taken by the X-ray CT apparatus 1 is a still image; however, the X-ray projection fluoroscopic image may be a video. For example, by continuously imaging the patient P in the X-ray fluoroscopy imaging mode, the imaging processing function 442 or 1442 of the X-ray CT apparatus 1 may be configured to acquire a plurality of consecutive pieces of projection data 91 in a time series such as a video.

In this situation, the display controlling function 447 or 1447 is configured to cause the display 42 to display the plurality of pieces of projection data 91 having been taken, as consecutive X-ray projection fluoroscopic images in a time series. The consecutive X-ray projection fluoroscopic images in the time series represent a video including a plurality of frames, for example.

Fourth Modification Example

Further, in the second to the fourth embodiments described above, the example was explained in which the rotating frame 13 rotates during the imaging process in the X-ray fluoroscopy imaging mode; however, the rotating frame 13 may be stopped during the imaging process in the X-ray fluoroscopy imaging mode.

The imaging processing function 1442 according to the present modification example is configured to image the patient P while the rotating frame 13 is rotating in the CT imaging mode and to image the patient P while the rotating frame 13 is stopped in the X-ray fluoroscopy imaging mode. The CT imaging mode is an example of the first imaging mode, whereas the X-ray fluoroscopy imaging mode is an example of the second imaging mode.

Further, in the present modification example, in the X-ray fluoroscopy imaging mode, the focal point position controlling function 448 adopts the FFS technique by which the focal point position of the X-rays is switched into the plurality of mutually-different positions. In other words, the configuration in which the rotating frame 13 is stopped during the imaging process in the X-ray fluoroscopy imaging mode like in the first embodiment may be combined with the configuration using the FFS scheme in the second to the fourth embodiments.

Fifth Modification Example

In the first embodiment described above, the super resolution process execution button 73 is displayed in the same mode, regardless of which mode is selected from between the X-ray fluoroscopy imaging mode and the CT imaging mode; however, the display mode of the super resolution process execution button 73 may be different between when the X-ray fluoroscopy imaging mode is selected and when the CT imaging mode is selected.

Sixth Modification Example

In the first embodiment described above, the user selects whether or not the super resolution processing function 444 is to perform the super resolution process; however, it is also acceptable to always have the super resolution process performed in the X-ray fluoroscopy imaging mode.

Seventh Modification Example

In the embodiments described above, the X-ray CT apparatus 1 is used as an example of the X-ray diagnosis apparatus; however, another modality may be used as an example of the X-ray diagnosis apparatus. For example, a Positron Emission Tomography (PET)-CT apparatus may serve as the X-ray diagnosis apparatus.

Further, in the embodiments described above, the X-ray detector 12 is described as being of an energy integrated type; however, the X-ray detector 12 may be a photon-counting X-ray detector. In other words, the configurations of the embodiments described above are also applicable to situations where the X-ray CT apparatus 1 is a photon-counting CT apparatus.

Eighth Modification Example

Further, in any of the embodiments described above, a part or all of the functions of the processing circuitry 44 of the X-ray CT apparatus 1 may be provided in an information processing apparatus such as a workstation.

Figure 17:
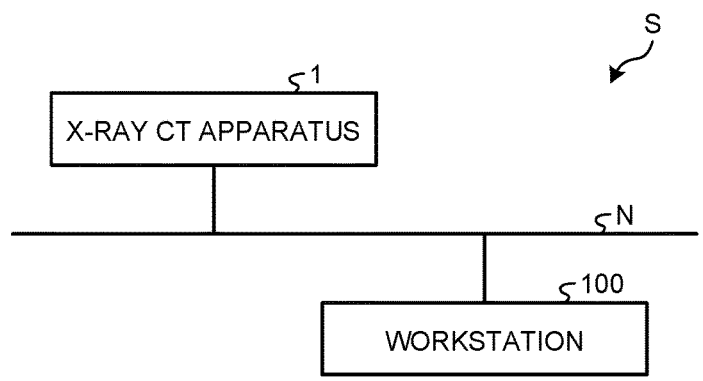
FIG. 17 is a diagram illustrating an example of a system including a workstation and an X-ray CT apparatus according to an eighth modification example.

FIG. 17 is a diagram illustrating an example of a system S including a workstation 100 and the X-ray CT apparatus 1 according to an eighth modification example. As illustrated in FIG. 17, the workstation 100 communicably connected to the X-ray CT apparatus 1 via a network N may execute the functions of the processing circuitry 44 according to any of the embodiments described above. The system S is an example of the medical image diagnosis system. The X-ray CT apparatus 1 is an example of the imaging apparatus. Further, the workstation 100 is an example of the medical image processing apparatus.

When the workstation 100 includes the processing circuitry 44, for example, the processing circuitry 44 includes an obtaining function configured to obtain, from the X-ray CT apparatus 1, projection data generated in the X-ray fluoroscopy imaging mode for obtaining an X-ray projection fluoroscopic image of a patient and CT image data generated in the CT imaging mode for obtaining a CT image of the patient. The obtaining function is an example of an obtaining unit. Further, the processing circuitry 44 of the workstation 100 according to the present embodiment includes the super resolution processing function 444 configured to perform the super resolution process on one of the projection data and the CT image data obtained from the X-ray CT apparatus 1. In this situation, the functions that can be included in the workstation 100 are not limited to these examples.

Further, possible examples of the medical image processing apparatus are not limited to the workstation 100. An information processing apparatus (e.g., an image processing server or a server apparatus provided in a cloud environment) other than the workstation 100 may be configured to execute a part of the functions included in the processing circuitry 44 according to any of the embodiments described above.

Ninth Modification Example

In the third and the fourth embodiments described above, the X-ray emission period is determined by the user operation; however, the X-ray emission period may be constant regardless of the duration of the user operation. In that situation, the user operation is an operation to input a time at which the X-ray emission is started, so that the X-ray emission ends after a prescribed time period has elapsed since the start time. In another example, the imaging processing function 1442 may be configured to end the X-ray emission when the focal point position controlling function 448 has moved the focal point position corresponding to a prescribed number of cycles or has moved a prescribed number of focal point positions since the start time.

Tenth Modification Example

In place of or in addition to any of the embodiments described above, it is acceptable to apply an image quality enhancing process (an image quality enhancing process using the super resolution process or the focal point control) on the projection data, both in the X-ray fluoroscopy imaging mode and in the CT imaging mode. In that situation, when the super resolution process is performed, because requirements on an image to be output eventually (an X-ray projection fluoroscopic image or a CT image) may vary, mutually-different trained models may be used in the super resolution process. In a modification example of the embodiments, a super resolution model to be applied to the projection data 91 obtained from an imaging process for an X-ray projection fluoroscopic image is a trained model trained by using, as input information and/or target information, images obtained under image taking conditions (e.g., X-ray tube current values, X-ray tube voltage values, gain values of the X-ray detector, settings for bundling pixels, image processing conditions, etc.) for taking X-ray projection fluoroscopic images. Further, a super resolution model to be applied to the projection data obtained from an imaging process for an X-ray CT image is a trained model trained by using, as input information and/or target information, projection data obtained under image taking conditions/scan conditions (e.g., X-ray tube current values, X-ray tube voltage values, gain values of the X-ray detector, settings for bundling pixels, projection data processing conditions, etc.) for obtaining X-ray CT images. The trained models for these types of projection data are stored in a memory or installed as hardware as separate models, so as to be used individually in the X-ray fluoroscopy imaging mode and in the CT imaging mode.

The super resolution processing function 444 of the X-ray CT apparatus 1 in the present modification example is configured to change the super resolution model to be used in the super resolution process in accordance with the imaging mode. More specifically, when the imaging processing function 442 imaged the patient P in the X-ray fluoroscopy imaging mode, the super resolution processing function 444 of the X-ray CT apparatus 1 according to the present modification example is configured to perform the super resolution process on the projection data 91, by using the super resolution model applied to the projection data 91 obtained from the imaging process for the X-ray projection fluoroscopic image described above. In contrast, when the imaging processing function 442 imaged the patient P in the CT imaging mode, the super resolution processing function 444 of the X-ray CT apparatus 1 according to the present modification example is configured to perform the super resolution process on the projection data, by using the super resolution model applied to the projection data obtained from the imaging process for the X-ray CT image described above.

In addition, in the CT imaging mode, the abovementioned super resolution model in the CT image domain may further be applied.

Eleventh Modification Example

Further, in the embodiments described above, when the imaging process is executed in the X-ray fluoroscopy imaging mode, the display controlling function 447 is configured to cause the display 42 to display the projection fluoroscopic image based on the projection data acquired in the X-ray fluoroscopy imaging mode. When the imaging process is executed in the CT imaging mode, the display controlling function 447 is configured to cause the display 42 to display the CT image reconstructed on the basis of the projection data acquired in the CT imaging mode. However, the display process is not requisite.

Figure 18:
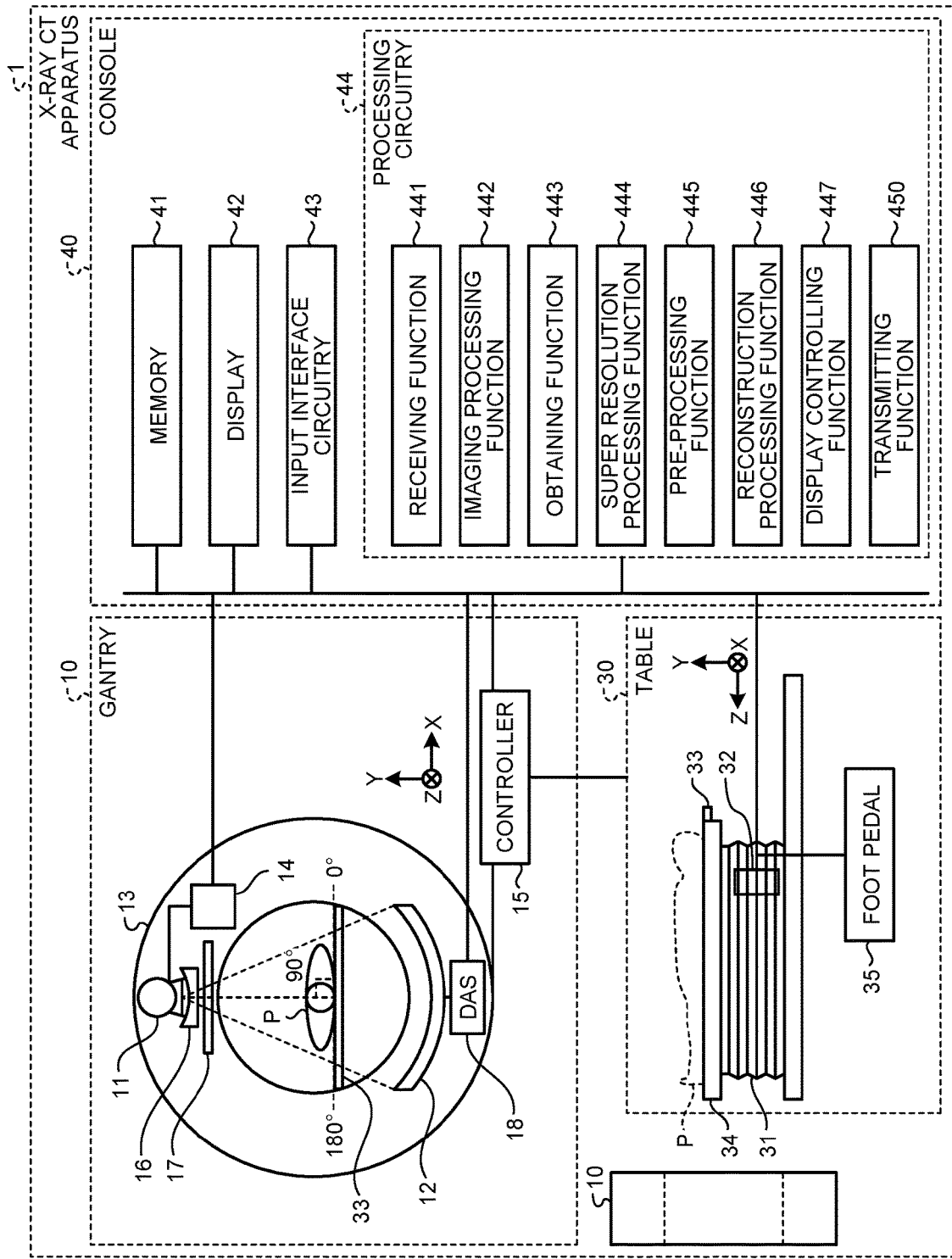
FIG. 18 is a diagram illustrating an exemplary configuration of an X-ray CT apparatus according to an eleventh modification example.

FIG. 18 is a diagram illustrating an exemplary configuration of the X-ray CT apparatus 1 according to an eleventh modification example. For example, as illustrated in FIG. 18, the processing circuitry 44 of the X-ray CT apparatus 1 may further include a transmitting function 450. The transmitting function 450 is an example of a transmitting unit and an output unit.

For example, when another information processing apparatus is configured to analyze the projection fluoroscopic image or the CT image, the transmitting function 450 is configured to transmit the projection fluoroscopic image or the CT image to the other information processing apparatus. Alternatively, the projection fluoroscopic image or the CT image may be displayed on the other information processing apparatus at the transmission destination. Further, the display realized by the display controlling function 447 and the transmission realized by the transmitting function 450 may both be implemented.

In this situation, the display realized by the display controlling function 447 and the transmission realized by the transmitting function 450 may collectively be referred to as "outputs".

Twelfth Modification Example

In the first embodiment described above, the imaging processing function 442 of the X-ray CT apparatus 1 is described as being configured, when the imaging process is to be executed in the CT imaging mode, to perform the position determining imaging process by using an imaging method different from that in the X-ray fluoroscopy imaging mode; however, the position determining imaging process is not requisite.

For example, the X-ray projection fluoroscopic image obtained in the X-ray fluoroscopy imaging mode may be used as an image for the position determining purpose, in place of a commonly-used position determining image. Alternatively, it is also acceptable not to use any position determining purpose image.

According to at least one aspect of the embodiments described above, the single X-ray CT apparatus is able to perform both the process of taking the CT image and the process of taking the high-precision X-ray projection fluoroscopic image.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

In relation to the embodiments described above, the following notes are presented as an aspect and selected characteristics of the present disclosure:

Note 1:
   An X-ray diagnosis apparatus including:
   an imaging system configured to perform an imaging process on an examined subject by emitting X-rays onto the examined subject; and
   a processing circuitry configured to execute the imaging process on the examined subject by controlling the imaging system in an imaging mode selected from between an X-ray fluoroscopy imaging mode for obtaining an X-ray projection fluoroscopic image of the examined subject and a Computed Tomography (CT) imaging mode for obtaining a CT image of the examined subject and configured to perform a super resolution process corresponding to the imaging mode.

Note 2:
   When the imaging process was executed in the X-ray fluoroscopy imaging mode, the processing circuitry may perform the super resolution process on projection data acquired by the imaging system.

Note 3:
   The processing circuitry may
   generate CT image data by reconstructing projection data acquired by the imaging system, and
   perform the super resolution process on the CT image data, when the imaging process was executed in the CT imaging mode.

Note 4:
   The processing circuitry may
   output a projection fluoroscopic image based on projection data acquired in the X-ray fluoroscopy imaging mode, for one or both of a display purpose and an analysis purpose, when the imaging process was executed in the X-ray fluoroscopy imaging mode, and
   output a CT image reconstructed on the basis of projection data acquired in the CT imaging mode, for one or both of a display purpose and an analysis purpose, when the imaging process was executed in the CT imaging mode.

Note 5:

The processing circuitry may receive an operation of a user to select a mode to be used for imaging the examined subject from between the X-ray fluoroscopy imaging mode and the CT imaging mode, and control the imaging system so as to image the examined subject by using one of the X-ray fluoroscopy imaging mode and the CT imaging mode, in accordance with the selection made by the user.

Note 6:

The processing circuitry may cause a display unit to display an X-ray fluoroscopy imaging mode selecting button capable of receiving an operation of the user to select the X-ray fluoroscopy imaging mode and a CT imaging mode selecting button capable of receiving an operation of the user to select the CT imaging mode.

Note 7:

The processing circuitry may receive an operation of the user to select whether or not the super resolution process is to be performed, and perform the super resolution process when the user selects to have the super resolution process performed.

Note 8:

The processing circuitry may cause a display unit to display a super resolution process execution button that is configured to receive an operation of the user to select whether or not the super resolution process is to be performed and that is displayed in a same mode regardless of which mode is selected from between the X-ray fluoroscopy imaging mode and the CT imaging mode.

Note 9:

The imaging system may include:

a negative pole configured to generate thermo electrons;

a positive pole configured to generate X-rays by receiving the thermo electrons emitted from the negative pole; and a thermo electron adjusting unit configured to adjust a track of the thermo electrons.

The processing circuitry may switch a focal point position of the X-rays into a plurality of mutually-different positions, by controlling the thermo electron adjusting unit while the imaging process is executed.

Note 10:

An X-ray diagnosis apparatus including:

an X-ray tube that includes a negative pole configured to generate thermo electrons, a positive pole configured to generate X-rays by receiving the thermo electrons emitted from the negative pole, and a thermo electron adjusting unit configured to adjust a track of the thermo electrons;

an X-ray detector configured to detect X-rays that were emitted from the X-ray tube and have passed through an examined subject; and a processing circuitry configured:

to execute the imaging process on the examined subject by controlling the X-ray tube and the X-ray detector;

to switch a focal point position of the X-rays into a plurality of mutually-different positions, by controlling the thermo electron adjusting unit while the imaging process is executed;

to generate combined projection data by combining together a plurality of pieces of projection data obtained by projecting images of the examined subject by using the X-rays emitted with the plurality of mutually-different focal point positions; and to cause a display unit to display the combined projection data as an X-ray projection fluoroscopic image.

Note 11:

The X-ray tube and the X-ray detector may be supported by a rotating frame that is rotatable.

The processing circuitry may cause the rotating frame to rotate at a time of the imaging process, and cause the X-ray tube to emit the X-rays, while the position of the X-ray tube supported by the rotating frame is within a prescribed range.

Note 12:

The processing circuitry may change the focal point position of the X-rays with prescribed timing synchronized with changes, with respect to the examined subject, of positions of the X-ray tube and the X-ray detector provided on the rotating frame that rotates.

Note 13:

The processing circuitry may receive an operation of the user to start emission of the X-rays, the X-ray tube and the X-ray detector may be supported by a rotating frame that is rotatable, and the processing circuitry may cause the rotating frame to rotate at a time of the imaging process, and cause the X-ray tube to emit the X-rays in accordance with timing with which the operation of the user to start the emission of the X-rays is received.

Note 14:

The processing circuitry may repeat, while a set in which a plurality of focal point positions are defined in prescribed order and in a prescribed quantity is regarded as one cycle, the switching of the focal point position of the X-rays as many times as a plurality of cycles, cause the rotating frame to rotate at a time of the imaging process, and cause the X-ray tube to start emitting the X-rays at a time when the focal point position of the X-rays is positioned, for the first time, in the first focal point position in a cycle after the operation of the user to start the emission of the X-rays is performed.

Note 15:

The processing circuitry may cause the X-ray tube to start emitting the X-rays at a time when the focal point position of the X-rays is switched for the first time, since the X-ray tube becomes able to emit the X-rays after the operation of the user to start the emission of the X-rays is performed.

Note 16:

The processing circuitry may causes, while the operation of the user to start the X-ray emission is continuously received, the X-ray tube to continue to emit the X-rays, and cause, when the operation of the user to start the X-ray emission has ended, the X-ray emission to end at a time when the focal point position of the X-rays switches from the last focal point position in a current cycle, to the first focal point position in a next cycle.

Note 17:

The X-ray tube and the X-ray detector may be supported by a rotating frame that is rotatable, the processing circuitry may execute a first imaging mode in which the examined subject is imaged while the rotating frame is rotating and a second imaging mode in which the examined subject is imaged while the rotating frame is stopped, and switch, in the second imaging mode, the focal point position of the X-rays into the plurality of mutually-different positions.

Note 18:

The processing circuitry may generate the combined projection data by combining together all the pieces of projection data obtained by projecting images of the examined subject from the start to the end of the X-ray emission.

Note 19:

When the time period of the X-ray emission by the X-ray tube starts at a time during a first cycle of the focal point position of the X-rays and ends at a time during a second cycle, the processing circuitry may generate the combined projection data by combining together a plurality of consecutive pieces of projection data, starting with a piece of projection data corresponding to the first focal point position in the time period of the X-ray emission among a plurality of focal point positions included in the first cycle and ending with a piece of projection data corresponding to the last focal point position in the time period of the X-ray emission among a plurality of focal point positions included in the second cycle.

Note 20:

The processing circuitry may generate, when a time period of the X-ray emission by the X-ray tube starts at a time during a first cycle of the focal point position of the X-rays and ends at a time during a second cycle, first combined projection data by combining together one or more pieces of projection data corresponding to one or more focal point positions falling in the time period of the X-ray emission among a plurality of focal point positions included in the first cycle, generate second combined projection data by combining together one or more pieces of projection data corresponding to one or more focal point positions falling in the time period of the X-ray emission among a plurality of focal point positions included in the second cycle, generate third combined projection data by combining the first combined projection data with the second combined projection data, and cause the display unit to display the third combined projection data as the X-ray projection fluoroscopic image.

Note 21:

The processing circuitry may continuously execute the imaging process on the examined subject, and cause the display unit to display a plurality of pieces of X-ray projection fluoroscopic image data having been taken, as the X-ray projection fluoroscopic image realized with consecutive X-ray projection fluoroscopic images in a time series.

Note 22:

The processing circuitry may perform the super resolution process on the combined projection data, and cause the display unit to display the combined projection data resulting from the super resolution process.

Note 23:

The processing circuitry may perform, when the imaging process is executed in the CT imaging mode, a position determining imaging process to obtain a position determining image used for setting an imaged range of a diagnosis-purpose CT image, and execute, in the position determining imaging process, the imaging process by using an imaging method different from that in the X-ray fluoroscopy imaging mode.

Note 24:

An X-ray diagnosis method including:

an imaging processing step of executing an imaging process on an examined subject by controlling an imaging system in an X-ray fluoroscopy imaging mode for obtaining an X-ray projection fluoroscopic image of the examined subject and in a CT imaging mode for obtaining a CT image of the examined subject; and a super resolution processing step of execution on a target of a super resolution process corresponding to which mode was used for imaging the examined subject between the X-ray fluoroscopy imaging mode and the CT imaging mode.

Note 25:

A non-transitory computer-readable medium including instructions that cause a computer to execute:

an imaging processing step of executing an imaging process on an examined subject by controlling an imaging system in an X-ray fluoroscopy imaging mode for obtaining an X-ray projection fluoroscopic image of the examined subject and in a CT imaging mode for obtaining a CT image of the examined subject; and a super resolution processing step of execution on a target of a super resolution process corresponding to which mode was used for imaging the examined subject between the X-ray fluoroscopy imaging mode and the CT imaging mode.

Note 26:

An X-ray diagnosis method including:

an imaging processing step of executing an imaging process on an examined subject, by controlling an imaging system so as to emit X-rays onto the examined subject;

a focal point position controlling step of switching a focal point position of the X-rays into a plurality of mutually-different positions, while the imaging process is executed;

a combining step of generating combined projection data by combining together a plurality of pieces of projection data obtained by projecting images of the examined subject by using the X-rays emitted with the plurality of mutually-different focal point positions; and a display step of causing a display unit to display the combined projection data as an X-ray projection fluoroscopic image.

Note 27:

A non-transitory computer-readable medium including instructions that cause a computer to execute:

an imaging processing step of executing an imaging process on an examined subject, by controlling an imaging system so as to emit X-rays onto the examined subject;

a focal point position controlling step of switching a focal point position of the X-rays into a plurality of mutually-different positions, while the imaging process is executed;

a combining step of generating combined projection data by combining together a plurality of pieces of projection data obtained by projecting images of the examined subject by using the X-rays emitted with the plurality of mutually-different focal point positions; and a display step of causing a display unit to display the combined projection data as an X-ray projection fluoroscopic image.

Note 28:

A medical image processing apparatus including a processing circuitry configured:

to obtain projection data generated in an X-ray fluoroscopy imaging mode for obtaining an X-ray projection fluoroscopic image of an examined subject and CT image data generated in a CT imaging mode for obtaining a CT image of the examined subject; and to perform a super resolution process corresponding to the imaging mode on one of the projection data and the CT image data.

Note 29:

A medical image processing method including:

an obtaining step of obtaining projection data generated in an X-ray fluoroscopy imaging mode for obtaining an X-ray projection fluoroscopic image of an examined subject and CT image data generated in a CT imaging mode for obtaining a CT image of the examined subject; and a super resolution processing step of performing a super resolution process corresponding to the imaging mode on one of the projection data and the CT image data.

Note 30:

A medical image diagnosis system including an imaging apparatus and a medical image processing apparatus in which the imaging apparatus includes:

an imaging system configured to perform an imaging process on an examined subject by emitting X-rays onto the examined subject; and a processing circuitry configured to execute the imaging process on the examined subject by controlling the imaging system in an imaging mode selected from between an X-ray fluoroscopy imaging mode for obtaining an X-ray projection fluoroscopic image of the examined subject and a CT imaging mode for obtaining a CT image of the examined subject, and the medical image processing apparatus is configured to perform a super resolution process corresponding to the imaging mode on one of the projection data and the CT image data obtained from the imaging apparatus.

Note 31:

An X-ray CT apparatus including:

a gantry that has, in a center part thereof, an opening having a substantially circular cylindrical shape and that includes an imaging system configured to perform an imaging process on an examined subject by emitting X-rays onto the examined subject; and a processing circuitry configured to execute the imaging process on the examined subject by controlling the imaging system in an imaging mode selected from between an X-ray fluoroscopy imaging mode for obtaining an X-ray projection fluoroscopic image of the examined subject and a CT imaging mode for obtaining a CT image of the examined subject and configured to perform a super resolution process corresponding to the imaging mode.

What is claimed is:

1. An X-ray diagnosis apparatus, comprising:

an imaging system configured to perform an imaging process on an examined subject by emitting X-rays onto the examined subject; and processing circuitry configured to receive an operation of a user to select a mode to be used for imaging the examined subject from between an X-ray fluoroscopy imaging mode for obtaining an X-ray projection fluoroscopic image of the examined subject and a Computed Tomography (CT) imaging mode for obtaining a CT image of the examined subject, receive an operation of the user to select whether or not a super resolution process is to be performed, execute the imaging process on the examined subject by controlling the imaging system in the X-ray fluoroscopy imaging mode or in the CT imaging mode in accordance with the selection made by the user, and perform the super resolution process corresponding to the X-ray fluoroscopy imaging mode or the CT imaging mode when the user selects to have the super resolution process performed.

2. The X-ray diagnosis apparatus according to claim 1, wherein, when the imaging process was executed in the X-ray fluoroscopy imaging mode, the processing circuitry is further configured to perform the super resolution process on projection data acquired by the imaging system.

3. The X-ray diagnosis apparatus according to claim 1, wherein the processing circuitry is further configured to:

generate CT image data by reconstructing projection data acquired by the imaging system, and perform the super resolution process on the CT image data, when the imaging process was executed in the CT imaging mode.

4. The X-ray diagnosis apparatus according to claim 1, wherein the processing circuitry is further configured to:

output a projection fluoroscopic image based on projection data acquired in the X-ray fluoroscopy imaging mode, for one or both of a display purpose and an analysis purpose, when the imaging process was executed in the X-ray fluoroscopy imaging mode, and output a CT image reconstructed based on projection data acquired in the CT imaging mode, for one or both of a display purpose and an analysis purpose, when the imaging process was executed in the CT imaging mode.

5. The X-ray diagnosis apparatus according to claim 1, wherein the processing circuitry is further configured to cause a display to display an X-ray fluoroscopy imaging mode selecting button capable of receiving an operation of the user to select the X-ray fluoroscopy imaging mode, and a CT imaging mode selecting button capable of receiving an operation of the user to select the CT imaging mode.

6. The X-ray diagnosis apparatus according to claim 1, wherein the imaging system includes:

a negative pole configured to generate thermo electrons;

a positive pole configured to generate X-rays by receiving the thermo electrons emitted from the negative pole; and a thermo electron adjusting unit configured to adjust a track of the thermo electrons, and the processing circuitry is further configured to switch a focal point position of the X-rays into a plurality of mutually-different positions, by controlling the thermo electron adjusting unit while the imaging process is executed.

7. The X-ray diagnosis apparatus according to claim 6, wherein the imaging system includes:
an X-ray tube including the negative pole, the positive pole, and the thermo electron adjusting unit; and
an X-ray detector configured to detect X-rays that were emitted from the X-ray tube and have passed through the examined subject, and
the processing circuitry is further configured to:
generate combined projection data by combining together a plurality of pieces of projection data obtained by projecting images of the examined subject by using the X-rays emitted with the plurality of mutually-different focal point positions, and
cause a display to display the combined projection data as an X-ray projection fluoroscopic image.

8. The X-ray diagnosis apparatus according to claim 7, wherein
the X-ray tube and the X-ray detector are supported by a rotating frame that is rotatable, and
the processing circuitry is further configured to:
cause the rotating frame to rotate at a time of the imaging process,
receive an operation of the user to start emission of the X-rays, and
cause the X-ray tube to emit the X-rays in accordance with timing with which the operation of the user to start the emission of the X-rays is received.

9. The X-ray diagnosis apparatus according to claim 8, wherein the processing circuitry is further configured to:
cause the rotating frame to rotate at a time of the imaging process,
repeat, while a set in which a plurality of focal point positions are defined in prescribed order and in a prescribed quantity is regarded as one cycle, the switching of the focal point position of the X-rays as many times as a plurality of cycles, and
cause the X-ray tube to start emitting the X-rays at a time when the focal point position of the X-rays is positioned, for a first time, in a first focal point position in a cycle after the operation of the user to start the emission of the X-rays is performed.

10. The X-ray diagnosis apparatus according to claim 8, wherein the processing circuitry is further configured to cause the X-ray tube to start emitting the X-rays at a time when the focal point position of the X-rays is switched for a first time, since the X-ray tube becomes able to emit the X-rays after the operation of the user to start the emission of the X-rays is performed.

11. The X-ray diagnosis apparatus according to claim 8, wherein the processing circuitry is further configured to:
cause, while the operation of the user to start the X-ray emission is continuously received, the X-ray tube to continue to emit the X-rays, and
cause, when the operation of the user to start the X-ray emission has ended, the X-ray emission to end at a time when the focal point position of the X-rays switches from a last focal point position in a current cycle, to a first focal point position in a next cycle.

12. The X-ray diagnosis apparatus according to claim 7, wherein
the X-ray tube and the X-ray detector are supported by a rotating frame that is rotatable, and
the processing circuitry is further configured to:
cause the rotating frame to rotate at a time of the imaging process, and
cause the X-ray tube to emit the X-rays, while a position of the X-ray tube supported by the rotating frame is within a prescribed range.

13. The X-ray diagnosis apparatus according to claim 12, wherein the processing circuitry is further configured to change the focal point position of the X-rays with prescribed timing synchronized with changes, with respect to the examined subject, of positions of the X-ray tube and the X-ray detector provided on the rotating frame that rotates.

14. The X-ray diagnosis apparatus according to claim 7, wherein
the X-ray tube and the X-ray detector are supported by a rotating frame that is rotatable, and
the processing circuitry is further configured to:
execute a first imaging mode in which the examined subject is imaged while the rotating frame is rotating and a second imaging mode in which the examined subject is imaged while the rotating frame is stopped, and
switch, in the second imaging mode, the focal point position of the X-rays into the plurality of mutually-different positions.

15. The X-ray diagnosis apparatus according to claim 7, wherein, when a time period of the X-ray emission by the X-ray tube starts at a time during a first cycle of the focal point position of the X-rays and ends at a time during a second cycle, the processing circuitry is further configured to generate the combined projection data by combining together a plurality of consecutive pieces of projection data, starting with a piece of projection data corresponding to a first focal point position in the time period of the X-ray emission among a plurality of focal point positions included in the first cycle and ending with a piece of projection data corresponding to a last focal point position in the time period of the X-ray emission among a plurality of focal point positions included in the second cycle.

16. The X-ray diagnosis apparatus according to claim 7, wherein the processing circuitry is further configured to:
generate, when a time period of the X-ray emission by the X-ray tube starts at a time during a first cycle of the focal point position of the X-rays and ends at a time during a second cycle, first combined projection data by combining together one or more pieces of projection data corresponding to one or more focal point positions falling in the time period of the X-ray emission among a plurality of focal point positions included in the first cycle,
generate second combined projection data by combining together one or more pieces of projection data corresponding to one or more focal point positions falling in the time period of the X-ray emission among a plurality of focal point positions included in the second cycle,
generate third combined projection data by combining the first combined projection data with the second combined projection data, and
cause the display to display the third combined projection data as the X-ray projection fluoroscopic image.

17. The X-ray diagnosis apparatus according to claim 7, wherein the processing circuitry is further configured to:
continuously execute the imaging process on the examined subject, and
cause the display to display a plurality of pieces of X-ray projection fluoroscopic image data having been taken, as the X-ray projection fluoroscopic image realized with consecutive X-ray projection fluoroscopic images in a time series.

18. An X-ray diagnosis method, comprising:
receiving an operation of a user to select a mode to be used for imaging an examined subject from between an X-ray fluoroscopy imaging mode for obtaining an X-ray projection fluoroscopic image of the examined subject and a Computed Tomography (CT) imaging mode for obtaining a CT image of the examined subject, receiving an operation of the user to select whether or not a super resolution process is to be performed, executing an imaging process on the examined subject by controlling an imaging system in the X-ray fluoroscopy imaging mode or in the CT imaging mode in accordance with the selection made by the user; and performing the super resolution process corresponding to the X-ray fluoroscopy imaging mode, or the CT imaging mode when the user selects to have the super resolution process performed.

* * * * *